(12) United States Patent
Yashima et al.

(10) Patent No.: US 10,481,106 B2
(45) Date of Patent: Nov. 19, 2019

(54) MEASUREMENT PROCESSING DEVICE, X-RAY INSPECTION DEVICE, MEASUREMENT PROCESSING METHOD, MEASUREMENT PROCESSING PROGRAM, AND STRUCTURE MANUFACTURING METHOD

(71) Applicant: NIKON CORPORATION, Tokyo (JP)

(72) Inventors: Hirotomo Yashima, Yokohama (JP); Fuminori Hayano, Tokyo (JP); Akitoshi Kawai, Yokohama (JP)

(73) Assignee: Nikon Corporation, Tokyo (JP)

(*) Notice: Subject to any disclaimer, the term of this patent is extended or adjusted under 35 U.S.C. 154(b) by 199 days.

(21) Appl. No.: 15/694,538

(22) Filed: Sep. 1, 2017

(65) Prior Publication Data

US 2018/0120243 A1 May 3, 2018

Related U.S. Application Data

(63) Continuation of application No. PCT/JP2015/056251, filed on Mar. 3, 2015.

(51) Int. Cl.
*G21K 5/08* (2006.01)
*G01N 23/083* (2018.01)
(Continued)

(52) U.S. Cl.
CPC ......... *G01N 23/083* (2013.01); *G01B 15/025* (2013.01); *G01B 15/045* (2013.01);
(Continued)

(58) Field of Classification Search
CPC .......... G01N 2223/419; G01N 23/083; G01N 23/046; G01N 23/18; G01B 15/025;
(Continued)

(56) References Cited

U.S. PATENT DOCUMENTS 5,848,115 A * 12/1998 Little ................... G01N 23/046
378/4
10,149,958 B1 * 12/2018 Tran ...................... A61M 21/00
(Continued)

FOREIGN PATENT DOCUMENTS

EP 0 875 751 A1 11/1998
EP 1 808 813 A2 7/2007
(Continued)

OTHER PUBLICATIONS

Notification of Reason(s) for Refusal dated Feb. 19, 2019 issued by the Japanese Patent Office in Japanese Application No. 2017-503257, and the English translation thereof.
(Continued)

*Primary Examiner* — Kiho Kim
(74) *Attorney, Agent, or Firm* — Finnegan, Henderson, Farabow, Garrett & Dunner, L.L.P.

(57) ABSTRACT

A measurement processing device used for an X-ray inspection device includes: a region information acquisition unit that acquires first region information based on X-rays passing through a first region that is a part of a first specimen; a storage unit that stores second region information related to a second region of a second specimen, the second region being larger than the first region; and a determination unit that determines whether or not a region corresponding to the first region is included in the second region, based on the first region information and the second region information.

20 Claims, 23 Drawing Sheets

(51) Int. Cl.
  *G01B 15/02* (2006.01)
  *G01N 23/18* (2018.01)
  *G01N 23/046* (2018.01)
  *G01B 15/04* (2006.01)
  *G06T 7/00* (2017.01)

(52) U.S. Cl.
  CPC .......... *G01N 23/046* (2013.01); *G01N 23/18* (2013.01); *G06T 7/0008* (2013.01); *G01B 2210/52* (2013.01); *G01N 2223/419* (2013.01); *G06T 2207/10116* (2013.01); *G06T 2207/30108* (2013.01)

(58) Field of Classification Search
  CPC .............. G01B 15/045; G01B 2210/52; G01B 2207/10116; G01B 2207/30108; A61B 6/12; G06T 7/0008
  See application file for complete search history.

(56) References Cited

U.S. PATENT DOCUMENTS

| | | | | |
|---|---|---|---|---|
| 2004/0081340 | A1* | 4/2004 | Hashimoto | A61B 8/00 382/128 |
| 2008/0205721 | A1* | 8/2008 | Udupa | G06K 9/6209 382/128 |
| 2010/0194749 | A1 | 8/2010 | Nightingale et al. | |
| 2013/0083896 | A1 | 4/2013 | Watanabe | |
| 2014/0270450 | A1* | 9/2014 | Grass | A61B 6/032 382/131 |
| 2014/0320408 | A1* | 10/2014 | Zagorsek | G06F 3/017 345/158 |
| 2015/0078640 | A1* | 3/2015 | Guo | G06T 7/11 382/131 |

FOREIGN PATENT DOCUMENTS

| | | |
|---|---|---|
| JP | 8-51131 | 2/1996 |
| JP | 11-30595 | 2/1999 |
| WO | WO 2016/035147 A1 | 3/2016 |
| WO | WO 2016/035148 A1 | 3/2016 |

OTHER PUBLICATIONS

International Search Report issued by the Japan Patent Office in corresponding International Application No. PCT/JP2015/056251, dated May 19, 2015 (3 pages).

Supplementary Partial European Search Report issued by the European Patent Office in European Application No. 15883924.1, dated Mar. 15, 2019.

Notification of Reasons for Refusal issued by Japanese Patent Office in counterpart Japanese Patent Application No. 2017-503257, dated Oct. 1, 2019.

\* cited by examiner

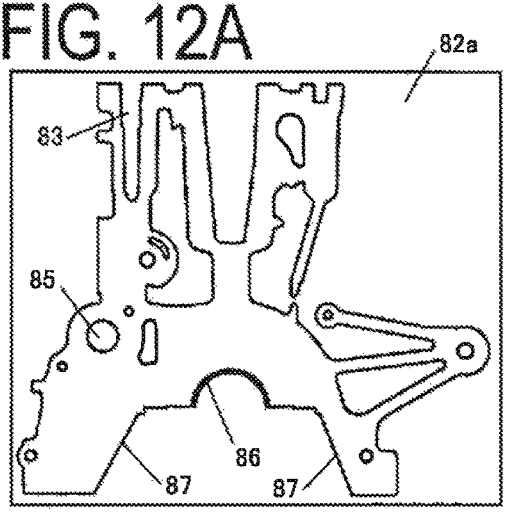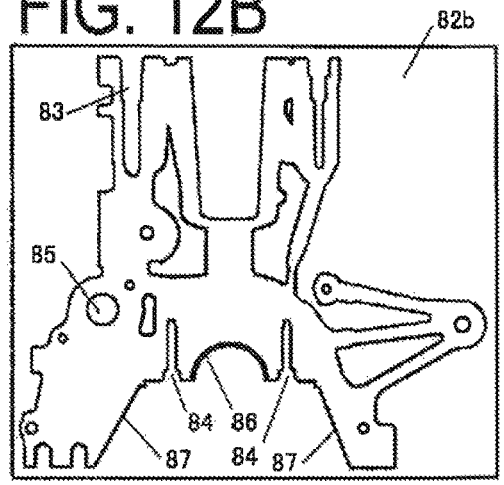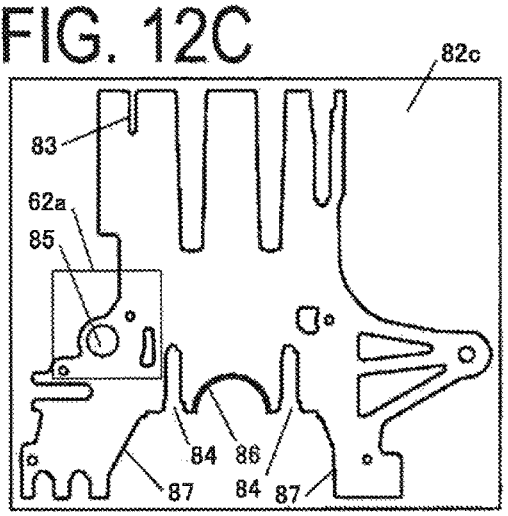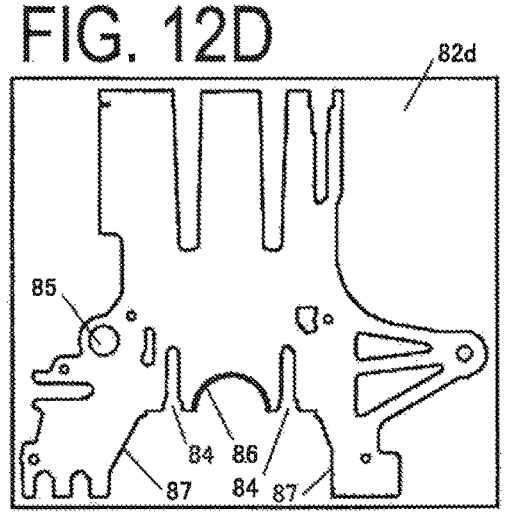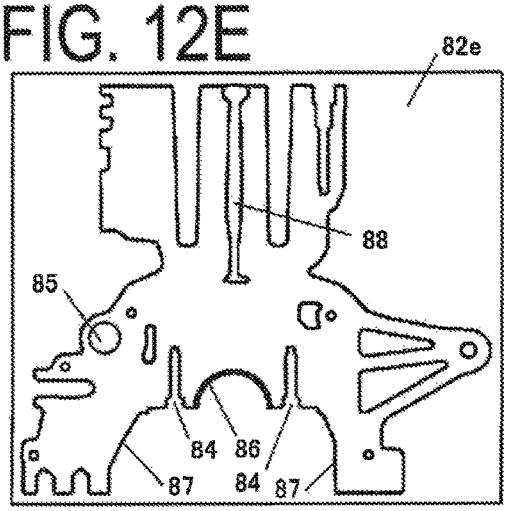

MEASUREMENT PROCESSING DEVICE, X-RAY INSPECTION DEVICE, MEASUREMENT PROCESSING METHOD, MEASUREMENT PROCESSING PROGRAM, AND STRUCTURE MANUFACTURING METHOD

INCORPORATION BY REFERENCE

This application is a continuation of international application No. PCT/JP2015/056251 filed Mar. 3, 2015.

The disclosures of the following priority applications are herein incorporated by reference: International application No. PCT/JP2015/056251 filed Mar. 3, 2015.

BACKGROUND OF THE INVENTION

1. Field of the Invention

The present invention relates to a measurement processing device, an X-ray inspection device, a measurement processing method, a measurement processing program, and a structure manufacturing method.

2. Description of Related Art

US 2013/0083896(A1) discloses that a technique for performing a comparison of a specimen with three-dimensional design data, and an evaluation of the thickness and internal defects of a specimen using an X-ray measurement device as an application of non-destructive internal inspection.

SUMMARY OF THE INVENTION

If a part and not the entire specimen is measured by an X-ray measurement device for a plurality of specimens manufactured under the same conditions, the same location for each of the plurality of specimens must be measured. However, if the specimen is a cast product for example, variations in shape may occur due to the influence of shrinking during molten metal being solidifies or the influence of wearing of a metal mold. Furthermore, recesses and protrusions are present on a casting surface before processing. Therefore, the height and inclination may be different for each of the specimens, and thus a problem occurs where the same region cannot be measured for the plurality of specimens. In particular, if a plane of a casting surface is brought into contact with a placement part, the problem becomes apparent.

(1) According to a first aspect of the present invention, a measurement processing device using an X-ray inspection device includes: a region information acquisition unit that acquires first region information based on X-rays passing through a first region which is a part of a first specimen; a storage unit that stores second region information related to a second region of a second specimen, which is larger than the first region; and a determination unit that determines whether or not a region corresponding to the first region is included in the second region, based on the first region information and second region information.

(2) According to a second aspect of the present invention, in the measurement processing device according to the first aspect, the first region preferably has a predetermined thickness including a predetermined cross section of the first specimen, and the second region is preferably thicker than the first region.

(3) According to a third aspect of the present invention, in the measurement processing device according to the second aspect, the first specimen and second specimen preferably have equivalent structures, and the second region information is preferably information based on design data expressing the structure of the second specimen.

(4) According to a fourth aspect of the present invention, in the measurement processing device according to the second aspect, the first specimen and second specimen preferably have equivalent structures, and the second region information is preferably information based on X-rays passing through the second region of the second specimen.

(5) According to a fifth aspect of the present invention, in the measurement processing device according to the second aspect, the first specimen and second specimen preferably have equivalent structures, and the second region information is preferably measurement information where a measurement inspection device other than the X-ray inspection device measures at least a part of the second region of the second specimen.

(6) According to a sixth aspect of the present invention, the measurement processing device according to the second aspect preferably further includes: a determination unit, where the second region information includes an inspection target region information related to an inspection target region of the first specimen, and the determination unit determines whether or not the first region information corresponds to the inspection target region information, based on the first region information and second region information.

(7) According to the seventh aspect of the present invention, the measurement processing device according to the sixth aspect preferably further includes: an evaluation unit that evaluates a condition of the first region based on the first region information, when the first region information is determined by the determination unit to correspond to the inspection target region information; and a positional difference calculation unit that calculates a positional difference between the first region and the inspection target region, based on the first region information and second region information, when the first region information is determined by the determination unit to not correspond to the inspection target region information.

(8) According to an eighth aspect of the present invention, a measurement processing device using an X-ray inspection device, includes: a storage unit that stores predetermined region information including an inspection target region of a specimen, and corresponding to a predetermined region larger than. the inspection target region; a region information acquisition unit that acquires region information related to a partial region of a specimen, based on X-rays passing through the partial region; and a determination unit that determines whether or not the partial region corresponds to the inspection target region, based on the region information and the predetermined region information.

(9) According to a ninth aspect of the present invention, in the measurement processing device according to the eighth aspect, the predetermined region information is preferably information based on design data expressing a structure of a specimen.

(10) According to a tenth aspect of the present invention, in the measurement processing device according to the eighth aspect, the predetermined region information is preferably information based on X-rays passing through the predetermined region of a specimen.

(11) According to an eleventh aspect of the present invention, in the measurement processing device according to the eighth aspect, the predetermined region information is preferably measurement information where a measurement inspection device other than the X-ray inspection device measures at least a part of the predetermined measurement region of a specimen.

(12) According to a twelfth aspect of the present invention, the measurement processing device according to the eighth aspect preferably further includes: an evaluation unit that evaluates a condition of the partial region based on the region information, when the partial region is determined by the determination unit to correspond to the inspection target region; arid a positional difference calculation unit that calculates a positional difference between the partial region and the inspection target region, based on the region information and predetermined region information, when the partial region is determined by the determination unit to not correspond to the inspection target region.

(13) According to a thirteenth aspect of the present invention, a measurement processing device using an X-ray inspection device includes: a region information acquisition unit that acquires region information related to a partial region of a specimen based on X-rays passing through the partial region; a standard information storage unit that stores standard information related to a partial region of a specimen; and a position identification unit that identifies a position of the partial region, based on the region information and standard information.

(14) According to a fourteenth aspect of the present invention, an X-ray inspection device includes: the measurement processing device according to the first aspect; an X-ray source that emits X-rays on a specimen; and a detection unit that detects X-rays passing through the specimen.

(15) According to a fifteenth aspect of the present invention, an X-ray inspection device includes: the measurement processing device according to the first aspect; an X-ray source that emits X-rays on a specimen; and a detection unit that detects X-rays passing through the specimen, where the first and second regions have different sizes in a direction orthogonal to a region surrounded by a light-emission point that is the X-ray source and a center of the detection unit.

(16) According to a sixteenth aspect of the present invention, an X-ray inspection device includes: the measurement processing device according to the seventh aspect; an X-ray source that emits X-rays on the first specimen; a detection unit that detects X-rays passing through the first specimen; and a positional relationship modification unit that modifies a positional relationship between the first specimen and X-ray source or detection unit, where the first region information is information based on detection results of the detection unit, and the positional relationship modification unit modifies the positional relationship such that the detection unit detects X-rays passing through the inspection target region, based on the positional difference calculated by the positional difference calculation unit, when the first region information is determined by the determination unit to not correspond to the inspection target region information.

(17) According to a seventeenth aspect of the present invention, an X-ray inspection device includes: the measurement processing device according to the twelfth aspect; an X-ray source that emits X-rays on a specimen; a detection unit that detects X-rays passing through a specimen; and a positional relationship modification unit that modifies a positional relationship between a specimen and X-ray source or detection unit, where the region information is information based on detection results of the detection unit, and the positional relationship modification unit modifies the positional relationship such that the detection unit detects X-rays passing through the inspection target region, based on the positional difference calculated by the positional difference calculation unit, when the partial region is determined by the determination unit to not correspond to the inspection target region.

(18) According to an eighteenth aspect of the present invention, a measurement processing device using an X-ray inspection device includes: a storage unit that stores predetermined region information including an inspection target region of a specimen, and corresponding to a predetermined region larger than the inspection target region; a first region information acquisition unit that acquires first region information based on X-rays passing through a first region which is a part of the specimen; and an identification unit that identifies a region corresponding to the inspection target region in the first region, based on the first region information and predetermined region information.

(19) According to a nineteenth aspect of the present invention, a measurement processing device using an X-ray inspection device includes: a storage unit that stores predetermined region information including an inspection target region of a specimen, and corresponding to a predetermined region larger than the inspection target region; a first region information acquisition unit that acquires first region information based on X-rays passing through a first region which is a part of the specimen; a first determination unit that determines whether or not the first region information includes inspection target region information related to the inspection target region, based on the first region information and predetermined region information; a second region information acquisition unit that acquires second region information, which is larger than the first region, based on X-rays passing through a second region including the first region, when the first region information is determined by the first determination unit to not include the inspection target region information;

and an extraction unit that extracts the inspection target region information from the second region information.

(20) According to a twentieth aspect of the present invention, an X-ray inspection device includes: the measurement processing device according to the seventh aspect; an X-ray source that emits X-rays on the first specimen; a detection unit that detects X-rays passing through the first specimen; and a detection range setting unit that sets a detection range of detecting X-rays passing through the first specimen by the detection unit, where the region information acquisition unit acquires the first region information based on X-rays passing through the first specimen, detected by the detection unit, arid the detection range setting unit sets a new detection range including the inspection target region, based on the positional difference calculated by the positional difference calculation unit, when the first region information is determined by the determination unit to not correspond to the inspection target region information.

(21) According to a twenty-first aspect of the present invention, a measurement processing method includes the steps of: acquiring first region information based on X-rays passing through a first region which is a part of a first specimen; and determining whether or not a region corresponding to the first region includes a second region, based on the first region information and second region information related to the second region of a second specimen, which is larger than the first region.

(22) According to a twenty-second aspect, a measurement processing method includes the steps of: acquiring first region information based on X-rays passing through a first region which is a part of a specimen; and determining whether or not the first region corresponds to an inspection target region, based on the first region information and predetermined region information corresponding to a predetermined region, which is larger than the inspection target region, including an inspection target region of a specimen.

(23) According to a twenty-third aspect of the present invention; a measurement processing method includes the steps of: acquiring region information related to a partial region based on X-rays passing through the partial region of a specimen; and identifying a position of the partial region in the specimen, based on the region information and standard information for identifying a position of the partial region in the specimen.

(24) According to a twenty-fourth aspect of the present invention, a measurement processing program executed by a computer includes: a region information acquisition process of acquiring first region information based on X-rays passing through a first region which is a part of a first specimen; and a determination process of determining whether or not a region corresponding to the first region includes a second region, based on the first region information and second region information related to the second region of a second specimen, which is larger than the first region.

(25) According to a twenty-fifth aspect of the present invention, a computer-readable computer program product containing a control program for measurement processing, the control program includes: instruction for a first region information acquisition process of acquiring first region information based on X-rays passing through a first region which is a part of a specimen; and instruction for a determination process of determining whether or not the first region corresponds to an inspection target region, based on the first region information and predetermined region information, which is larger than the inspection target region, corresponding to a predetermined region including an inspection target region of a specimen.

(26) According to a twenty-sixth aspect of the present invention, a computer-readable computer program product containing a control program for measurement processing, the control program includes: instruction for a region information acquisition process of acquiring region information related to a partial region based on X-rays passing through the partial region of a specimen; and instruction for an identification process of identifying a position of the partial region in the specimen, based on the region information and standard information for identifying a position of the partial region in the specimen.

(27) According to a twenty-seventh aspect of the present invention, a structure manufacturing method includes the steps of: creating design information related to a structure shape; creating the structure based on the design information; acquiring shape information by measuring the shape of the created structure, using the measurement processing device according to the first aspect; and comparing the design information and shape information acquired above.

(28) According to the twenty-eighth aspect of the present invention, a measurement processing device using an X-ray inspection device includes: a region information acquisition unit that detects X-rays passing through a partial region of a first specimen and acquires first region information related to a first region; an inclination detection unit that detects an inclination of the first specimen when acquiring the first region information; and a comparison unit that compares a standard inclination and the inclination of the first specimen detected by the inclination detection unit.

(29) According to the twenty-ninth aspect of the present invention, in the measurement processing device according to the twenty-eighth aspect, the region information acquisition unit preferably detects X-rays passing through a partial region of a second specimen, and acquires second region information related to a second region, the inclination detection unit preferably detects an inclination of the second specimen when acquiring the second region information, and the comparison unit preferably compares the inclination of the second specimen and the inclination of the first specimen detected by the inclination detection unit.

(30) According to a thirtieth aspect of the present invention, in the measurement processing device according to the twenty-eighth aspect, the inclination detection unit preferably detects an inclination of the first specimen when acquiring the first region information, based on the first region information.

An object of the aspects of the present invention is to provide a measurement processing device, an X-ray inspection device, a measurement processing method, a measurement processing program, and a structure manufacturing method, which can suppress detection failure.

BRIEF DESCRIPTION OF THE DRAWING

FIGS. 12A to 12E are diagrams schematically illustrating a reconstruction image obtained by performing an X-ray inspection for a plurality of sliced planes while gradually changing the slice position.

DESCRIPTION OF EMBODIMENTS

—First Embodiment—

Figure 1:
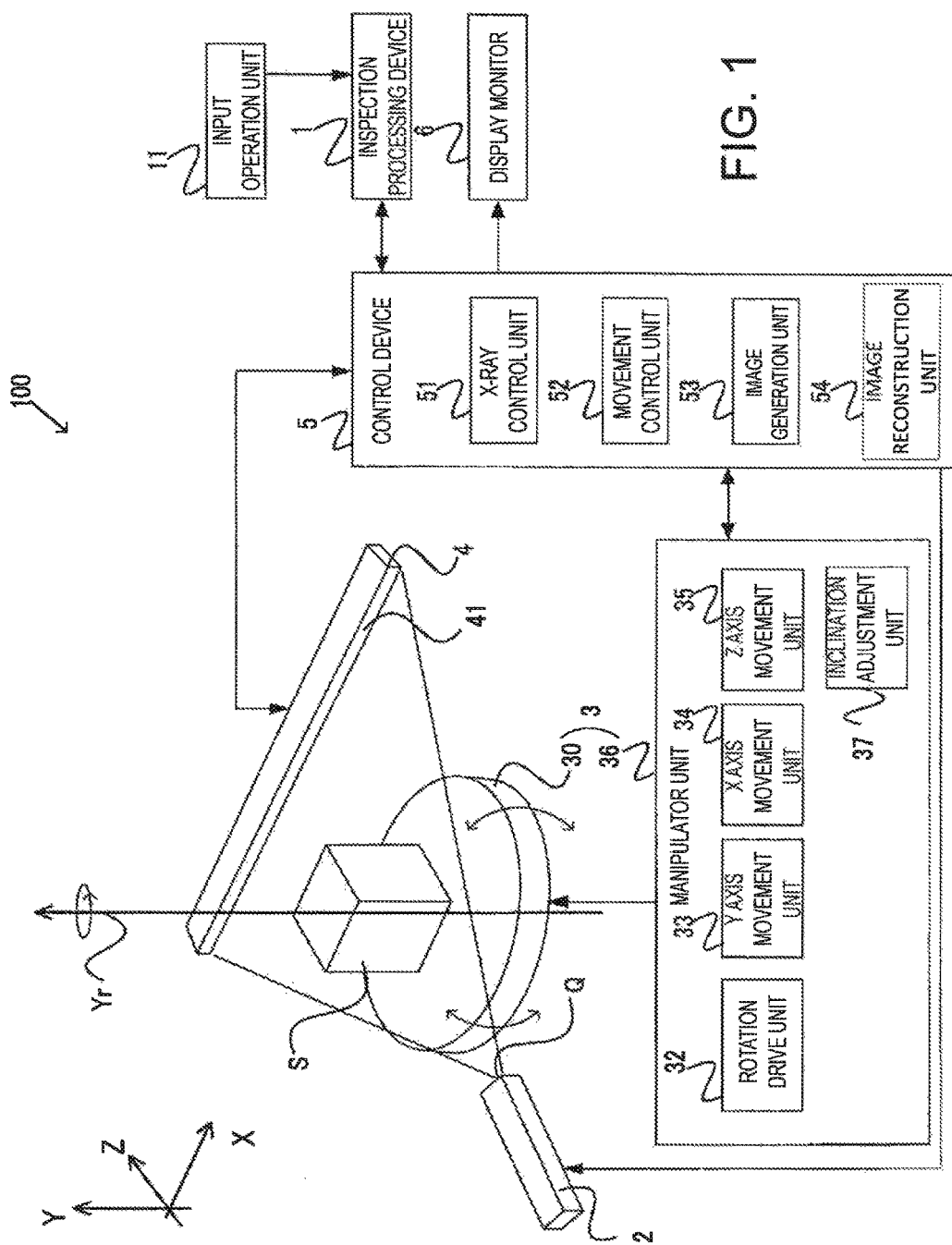
FIG. 1 is a diagram schematically illustrating an example of a configuration of an X-ray inspection device of a first embodiment.

An X-ray inspection device and an inspection processing device for an X-ray inspection device will be described according to a first embodiment of the present invention while referring to the drawings. The X-ray inspection device non-destructively acquires internal information (for example, the internal structure) or the like of a specimen by emitting X-rays at the specimen and detecting the transmitted X-rays passing through the specimen. The present embodiment will be described by providing an example where an X-ray inspection device is used as an internal inspection device for acquiring internal information about a cast product such as an engine block or the like and performing quality management or the like thereof.

Note that an X-ray inspection device 100 is not limited to a cast Product such as an engine block, and may also acquire shape information for the internal structure of a resin molded product or a joint part formed when respective members have been joined using adhesive or welding, and may be used to perform inspection therefor.

Furthermore, the present embodiment is for specifically describing the gist of the invention in order to facilitate understanding, and does not limit the present invention unless otherwise specified.

FIG. 1 is a diagram schematically illustrating an example of a configuration of the X-ray inspection device 100 according to the embodiment. Note that for convenience of description, a coordinate system including an X axis, a Y axis, and a Z axis is set as is illustrated in the drawing.

The X-ray inspection device 100 is provided with an inspection processing device 1, an X-ray source 2, a placement unit 3, a detector 4, a control device 5, a display monitor 6, and an input operation unit 11. Note that the inspection processing device 1 that is configured separately from the X-ray inspection device 100 is included in one aspect of the present invention. The X-ray source 2, placement unit 3, and detector 4 are stored inside a housing (not illustrated in the drawing) disposed such that an XZ plane is substantially horizontal on a floor surface of a factory or the like. The housing includes lead as a material to preventing X-rays from leaking to the outside.

The X-ray source 2 emits X-rays in a fan shape (a so-called "fan beam") in the Z axis+ direction along an optical axis Zr parallel to the Z axis with an emission point Q illustrated in FIG. 1 as the vertex, based on control by the control device 5. The emission point Q corresponds to a focal spot of the X-ray source 2. In other words, the optical axis Zr connects the emission point Q which is a focal spot of the X-ray source 2, and a center of an image capturing region of the detector 4 described later. Note that for the X-ray source 2, instead of emitting X-rays in a fan shape, X-rays emitted in a cone shape (a so-called "cone beam") is also included in one aspect of the present invention. The X-ray source 2 can emit at least one of approximately 50 eV ultrasoft X-rays, approximately from 0.1 to 2 keV soft X-rays, approximately from 2 to 20 keV X-rays, approximately from 20 to 100 keV hard X-rays, and X-rays having an energy of 100 keV or higher, for example.

The placement unit 3 is provided with a placement stage 30 on which a specimen S is placed, and a manipulator unit 36 made from a rotation drive unit 32, a Y axis movement unit 33, an X axis movement unit 34, a Z axis movement unit 35, and an inclination adjustment unit 37, and provided more in a Z axis+ side than the X-ray generation unit 2. The placement stage 30 is provided to be rotatable by the rotation drive unit 32, and when the rotation axis Yr moves in the X, Y, or Z directions based on the rotation drive unit 32, the placement stage 32 also moves therewith. Furthermore, an inclination with regard to an XZ plane of the placement stage 30, in other words, an angle formed between rotation axis Yr and an upper surface of the placement stage 30 can be adjusted by the inclination adjustment unit 37.

The rotation drive unit 32 is configured by an electric motor or the like for example, and rotates the placement stage 30 with an axis that is parallel and passes through a center of the placement unit 30 as a rotational axis Yr by a rotational force generated by an electric motor controlled and driven by the control device 5, described later. The Y axis movement unit 33, the X axis movement unit 34, the Z axis movement unit 35, and the inclination adjustment unit 37 are controlled by the control device 5 to respectively move the placement stage 30 in the X direction, the Y direction, and the Z direction, and change the inclination with regard to the XZ plane of the placement stage 30, such that the specimen S is positioned in the emission range of the X-rays emitted by the X-ray generation unit 2. Furthermore, the Z axis movement unit 35 is controlled by the control unit 5 to move the placement stage 30 in the Z direction such that the distance from the X-ray source 2 to the specimen S is a distance where the specimen S in the captured image is at a desired magnification ratio.

The detector 4 is provided more in the Z direction+ side than the X-ray source 2 and the placement stage 30. In other words, the placement stage 30 is provided between the X-ray source 2 and the detector 4 in the Z direction. The detector 4 is a so-called line sensor having an incidence surface 41 extending in the X direction on a plane parallel to the XY plane, and X-rays including transmitted X-rays passing through the specimen S placed on the placement stage 30, emitted from the X-ray source 2 are incident onto the incidence surface 41. The detector 4 is configured by a scintillator unit including a well-known scintillating substance, a photomultiplier tube, a light reception unit, and the like. The detector 4 converts the energy of X-rays incident on the incidence surface 41 of the scintillator unit into light energy such as visible light, ultraviolet light, or the like, amplifies the energy using the photomultiplier tube, converts the amplified light energy into electrical energy using the light reception unit, and outputs the energy as an electrical signal to the control device 5.

Note that the detector 4 may convert the energy of incident X-rays to electrical energy, and output the energy as an electrical signal without converting into light energy. The detector 4 has a structure where the scintillator unit, the photomultiplier tube, and the light reception unit are divided into a plurality of pixels. Thereby, an intensity distribution of X-rays which have been emitted from the X-ray source 2 and have passed through the specimen S can be acquired. Note that the detector 4 may have a structure where the scintillator unit is directly formed on the light reception unit (photoelectric conversion unit) without providing a photomultiplier tube.

Note that the detector 4 is not limited to a line sensor, and may be a two-dimensional plane detector. In other words, in the present embodiment, a line sensor of the detector 4 has an incidence surface 41 extending in the X direction on a plane parallel to the XY plane, but only one incidence surface 41 is disposed in the Y direction. Furthermore, in the XY plane, a plurality of incidence surfaces 41 are disposed in the X direction. Furthermore, each of the plurality of incidence surfaces 41 can independently detect the intensity of the X-rays. In the present embodiment, a plurality of the incidence surfaces 41 may be aligned in the Y direction. For example, in the XY plane in FIG. 1, the detector may be a two-dimensional plane detector where a plurality of incidence surfaces 41 are disposed in the X direction and the Y direction, Furthermore, if a two-dimensional plane detector is used, only an incidence surface 41 in the X direction at a predetermined position in the Y direction is used among the plurality of incidence surfaces 41 aligned in the Y direction, which may be used as a line sensor. In this case, an intensity distribution of the X-rays on the incidence surfaces 41 in the X direction at a predetermined position in the Y direction may be acquired, and shape information for the specimen S may be analyzed from the intensity distribution of the X-rays acquired at the predetermined position in the Y direction. Furthermore, in this case, when acquiring an intensity distribution of the X-rays on the incidence surfaces 41 in an X direction at a plurality of positions in the Y direction, an intensity distribution for X-rays on the incidence surfaces 41 in the X direction at positions that are mutually separated in the Y direction may be acquired.

The X-ray source 2, placement unit 3, and detector 4 are supported by a frame (not illustrated in the drawings). The frame is manufactured with sufficient rigidity. Therefore, the X-ray source 2, placement stage 3, and detector 4 can he stably supported while acquiring a projected image of the specimen S. Furthermore, the frame is supported by an anti-vibration mechanism (not illustrated in the drawings), and thus vibrations generated on the outside are prevented from transmitting as is to the frame.

The input operation unit 11 is configured by a keyboard, various buttons, a mouse, and the like, and is operated by an operator when inputting an inspection target region position at the time of the inspection of the specimen S as described later or updating an inspection target region. When the input operation unit 11 is operated by an operator, an operation signal corresponding to the operation is output to the inspection processing device 1.

The control device 5 has a microprocessor, peripheral circuit thereof, and the like, and controls various units of the X-ray inspection device 100 by reading and executing a control program stored in advance on a storage medium not illustrated in the drawings (such as a flash memory or the like). The control device 5 is provided with an X-ray control unit 51, a movement control unit 52, an image generation unit 53, and an image reconstruction unit 54. The X-ray control unit 51 controls an operation of the X-ray source 2, and the movement control unit 52 controls a movement operation of the manipulator 36. The image generation unit 53 generates X-ray generates X-ray projected image data-of the specimen S based on an electrical signal output from the detector 4, and the image reconstruction unit 54 generates a reconstruction image by performing a known image reconstruction process, based on the projected image data of the specimen S with different projection directions while controlling the manipulator unit 36. Furthermore, in the present embodiment, three-dimensional shape information which is the internal structure of the specimen S is generated by a surface model construction unit provided inside the image reconstruction unit 54 based on the reconstruction image acquired at different positions in the Y direction. In this case, the image reconstruction process includes back projection methods, filtered back projection methods, iterative reconstruction methods, and the like.

When performing inspection of the internal structure of the specimen S, the X-ray inspection device 100 moves the placement stage 30 in XYZ directions, and adjusts the inclination angle of the placement stage 30 to position the specimen S at an inspection position. Furthermore, the X-ray inspection device 100 emits a slit beam having a predetermined width in the Y direction from the X-ray source 2 towards the specimen S being rotated based on a rotational drive of the placement stage 30. The detector 4 receives the transmission X-rays including X-rays passing through the specimen S, and obtains shape information for a cross section of the specimen S corresponding to the width (such as approximately 1 mm) in the Y direction of the slit beam. The X-ray inspection device 100 repeatedly performs emission of the slit beam towards the specimen S during rotational drive, and movement of the placement stage 30 in the Y direction, in other words, the movement of the specimen S in the Y direction. When the slit beam is performed within a range extending to an entire region of the length in the Y direction of the specimen S placed on the placement stage 30, shape information for the entire specimen S can be generated (hereinafter, referred to as a full scan). When emission of the slit beam is performed within a range of a part of the length in the Y direction of the specimen S placed on the placement stage 30, the transmission image for the portion can be acquired and shape information for a part of the specimen S can be generated based on the transmission image (hereinafter, referred to as a partial scan).

Note that in the present specification, a region in which the slit beam overlaps with the specimen S is referred to as a sliced plane in the following description. In the present embodiment, when the specimen S is disposed in a region defined by the emission point Q and the incidence surface 41 of the detector 4, X-rays passing through the specimen S can be detected. In this case, the detectable region of X-rays passing through the specimen S is referred to as a sliced plane. The sliced plane is a region having a predetermined width. Note that in the present embodiment, a region where the specimen S and the region defined by the incidence surface 41 of the detector 4 and the emission point Q are superimposed is the sliced plane. Of course, the sliced plane may be a region connecting the emission point Q and a center of the detector 4, for example. The position of the sliced plane with regard to the specimen S on the placement stage 30 relatively moves in the Y direction with the movement of the placement stage 30 in the Y direction. In the following description, the relative movement of the sliced plane with regard to the specimen S is referred to as displacement, and the amount of movement at this time is referred to as the displacement amount. Note that in the present embodiment, when the placement stage 30 is moved in the Y direction after detecting a predetermined region in a predetermined position, the predetermined region detected prior to the movement and a predetermined region detected after the movement are not superimposed. Of course, the regions may be partially superimposed. In the present embodiment, the placement stage 30 is moved in a direction intersecting with regard to a region surrounded by the center of the detector 4 and the emission point Q of the X-ray source 2. Thereby, a region that could not be detected prior to the movement can be detected based on the movement of the placement stage 30. For example, in the present embodiment, a region surrounded by the center of the detector 4 and emission point Q of the X-ray source 2 is parallel to an XZ plane. Therefore, the placement stage 30 is moved along the Y direction as the direction intersecting the XZ plane at 90°. Of course, the intersecting direction is not limited to 90°, and may be 10°, 20°, 30°, 40°, 50°, 60°, 70°, or 80°, for example.

The X-ray inspection device 100 in the present embodiment performs inspection by performing a full scan or a partial scan with regard to a plurality of the specimens having similar same shape such as in a cast product, for example. The full scan refers to a measurement operation for generating a reconstruction image at a predetermined interval in the Y direction, in order to acquire the interior structure of the entire specimen S. The scan is performed at an opportunity where a relatively large amount of time can be assigned to inspection time when mass-production manufacturing is not performed, such as after maintenance of a metal mold for manufacturing the specimen S. The partial scan refers to a measurement operation for generating a reconstruction image for only a part including an evaluation region described later of the specimens S. Other than the timing for performing the full scan, the partial scan is performed when a part (hereinafter, referred to as evaluation region) with a high possibility of an internal defect occurring for a plurality of specimens S is selected as an inspection target region and then inspected.

As illustrated in the block diagram in FIG. 2, the inspection processing device 1 has a microprocessor, peripheral circuit thereof, and the like, and reads and executes a control program stored in advance in a storage medium (such as a flash memory or the like) not illustrated in the drawings to perform various processes when inspecting a part of the specimen S described later. The inspection processing device 1 is provided with a control unit 110, configuration information acquisition unit 111, region information acquisition unit 112, comparison unit 113, positional difference calculation unit 114, inspection range setting unit 115, evaluation unit 116, data accumulation unit 117, inspection unit 118, and evaluation region setting unit 119.

The control unit 110 controls each unit of the inspection processing device 1 described below, and also controls each unit of the X-ray inspection device 100 through the control device 5. The configuration information acquisition unit 111 acquires shape information of the specimen S obtained by setting design information such as CAD or the like related to the specimen S. The region information acquisition unit 112 acquires shape information for a predetermined region obtained by the partial scan. Three-dimensional shape information of the predetermined region acquired by the region information acquisition unit 112 is hereinafter referred to as region information. The comparison unit 113 compares master data M with the region information acquired by the region information acquisition unit 112. The master data M is described later. The positional difference calculation unit 114 calculates a difference between a position of the specimen S corresponding to the acquired region information and a position of a region to be inspected in the specimen S, based on comparison results by the comparison unit 113. The inspection range setting unit 115 sets a region including an evaluation region set by the evaluation region setting unit 119 described later as a region where the specimen S is partially to be scanned (hereinafter, referred to as a partial scan region).

The evaluation unit 116 evaluates the quality of the specimen S based on the region information acquired by partial scan on the specimen S. The data accumulation unit 117 is a non-volatile storage medium for storing various data generated by processes by the aforementioned units of the inspection processing device 1. The inspection unit 118 generates internal information based on partial scan data. The evaluation region setting unit 119 performs an evaluation region setting process of setting an evaluation region for performing inspection during a partial scan on the specimen S, using information or the like based on the design information acquired by the configuration information acquisition unit 111. A master data generation unit 120 generates master data M based on information acquired by the configuration information acquisition unit 111 and region information acquisition unit 112. Master data M is information expressing a shape for at least a part of the specimen S, and details thereof will be described later.

Note that the details of the aforementioned units of the inspection processing device 1 will be described later.

—Positioning of the Specimen S—

When the plurality of specimens S are sequentially inspected, the same regions of the specimens S is required to be scanned for all of the specimens S, and therefore, the specimen S is required to be accurately positioned with regard to a device coordinate system of the X-ray inspection device 100.

However, as described above, variations occur in the shapes of the specimens S, and therefore, the height or inclination of the specimens placed on the placement unit 30 may differ.

Therefore, in the present embodiment, when the evaluation region is scanned, the partial scan is temporarily performed on the specimen S placed on the placement stage 30, and the results thereof are compared with the master data M described later to determine whether or not the specimen S is accurately positioned with regard to the position coordinate system. Specific descriptions are provided below. Note that in the following description, the term "position" is a concept which also includes "inclination". For example, the position of the specimen includes a position on an XZ plane of the specimen S in the device coordinate system, height in the Y direction, and inclination of the specimen S with regard to the device coordinate system. Furthermore, in the following description, the inclination of the specimen S with regard to the device coordinate system may simply be referred to as inclination, or referred to as posture of the specimen S.

—Master Data M—

The master data M will be described while referring to FIG. 3 to FIG. 10. The master data M is information related to the shape of a region of at least a part of the specimen S, and is used for determining which part of the specimen S was partially scanned. The master data M includes information related to the position of the evaluation region. The master data M is data having redundancy in a width in the Y direction, and therefore, even if the specimen S when placed on the placement stage 30 deviates in the Y direction or is inclined, a part on which the partial scan is performed can be identified in the subject S. In the following description, a width in the Y direction of the master data M, the partial scan region, or the like is also referred to as thickness.

Figure 3:
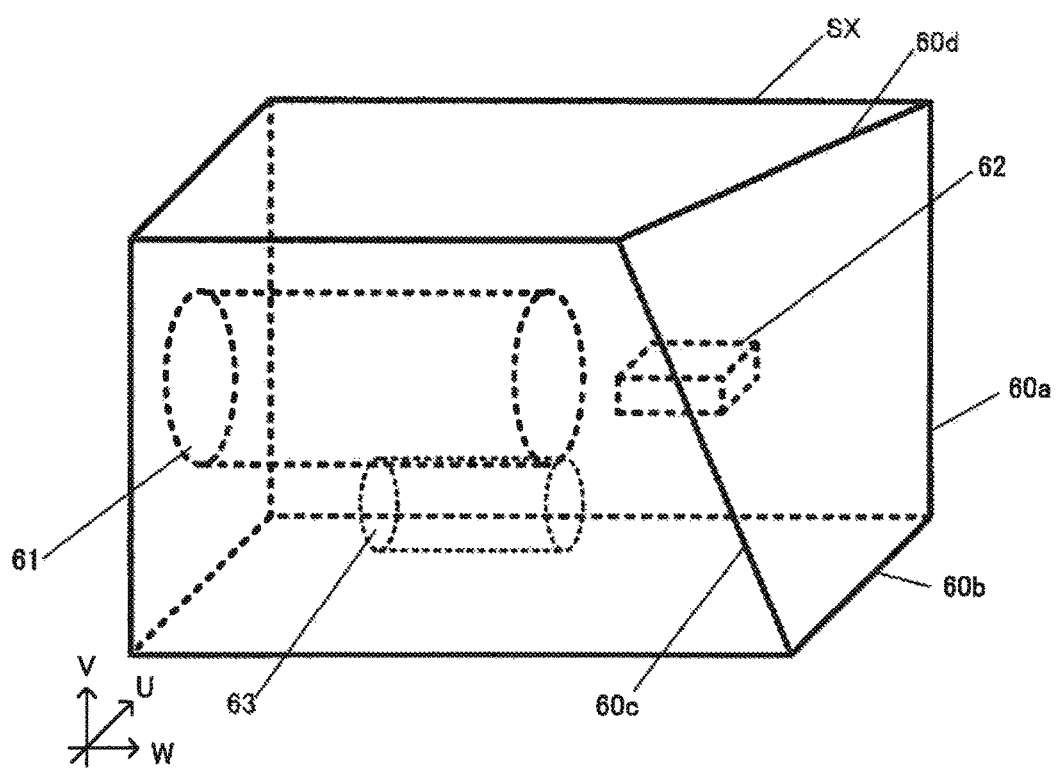
FIG. 3 is a diagram schematically illustrating a specimen for describing master data.

For convenience of description, the specimen S has a shape as illustrated in FIG. 3. A specimen SX illustrated in FIG. 3 is hypothesized to have a hexahedral shape. Furthermore, for convenience of description, a coordinate system including a U axis, a V axis, and a W axis with regard to the specimen SX is set as is illustrated in the drawing. A surface on a right side of the drawing of the. specimen SX is not parallel to a UV plane, and of sides 60a, 60b, 60c, and 60d on a right side of the drawing, the side 60a on a far side of the drawing is parallel to the V axis, and the side 60b on a lower side of the drawing is parallel to the U axis. The side 60c on a front side of the drawing is inclined so as to face the W axis– direction when facing the axis V+ direction, and the side 60d on an upper side of the drawing is inclined so as to face the W axis+ direction when facing the U axis+ direction. Furthermore, a cylindrical hole portion 61 extending in the W axis+ direction from a surface on a left side of the drawing is provided. The hole portion 61 does not penetrate in the W axis+ direction. Note that a rectangular body denoted by reference numeral 62 represents the evaluation region. Furthermore, a cylinder denoted by reference numeral 63 represents a member cast into the specimen S (hereinafter, referred to as cast member). The cast member is a material that is different from peripheral material, and therefore, the absorption rate of X-rays is normally different from peripheral material. Herein, a cast iron member is cast in aluminum.

Figure 4:
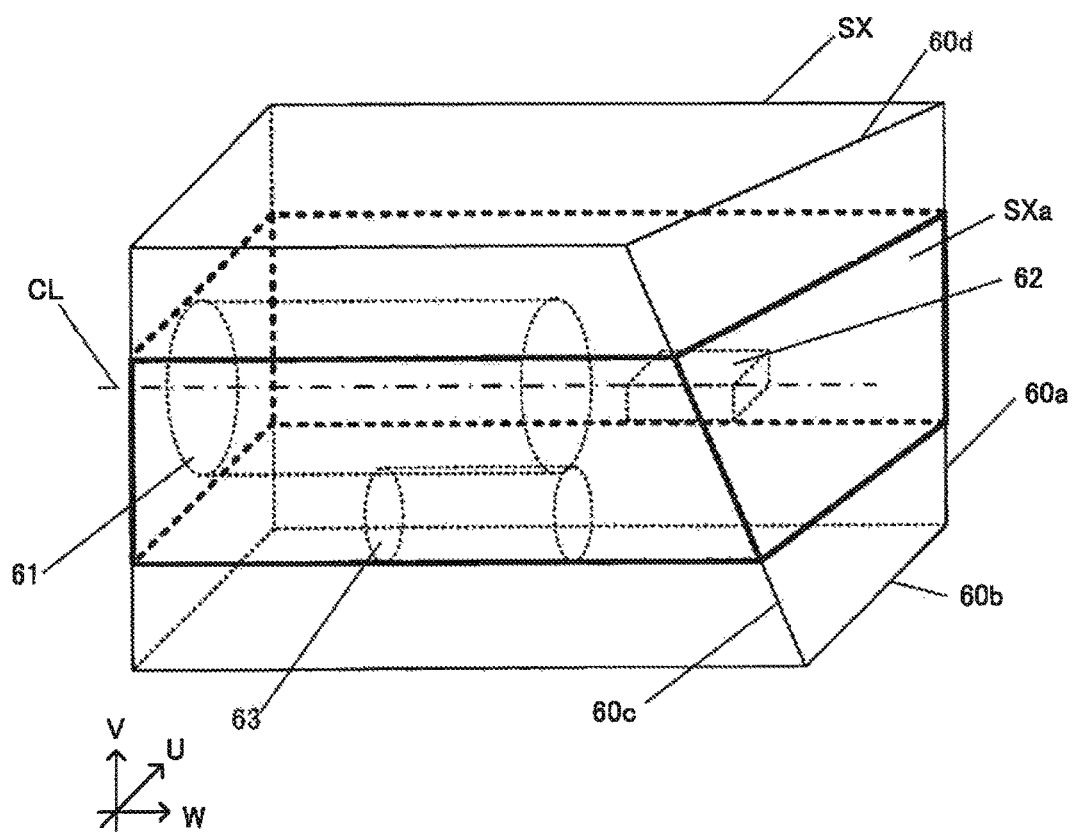
FIG. 4 is a diagram illustrating a region of the master data.
Figure 5:
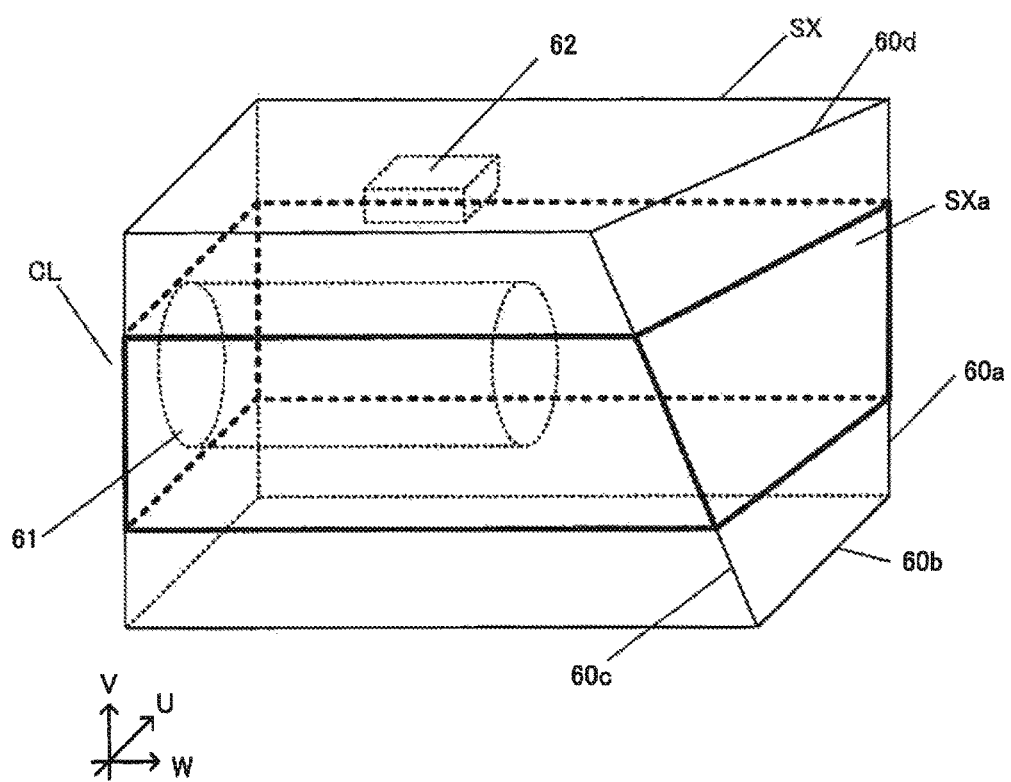
FIG. 5 is a diagram illustrating a region of the master data.

The master data M of the specimen SX is data related to the shape of a region SXa that is a part of the specimen SX, expressed by a thick line in FIG. 4, for example. Note that the master data M may be data related to the shape of the entire specimen SX. For example, information expressing an outline of the region SXa, information expressing a shape of the hole portion 61, information expressing a position of the hole portion 61 in the region SXa, information related to a shape of the evaluation region 62, information for a position of the evaluation region 62 in the region SXa, information for a position of the region SXa in the specimen SX, in other words, information expressing a range of the region SXa, and the like correspond to the master data M, but the information is not all required to be included. Note that the region SXa is not required to include the evaluation region 62, and if information for the positional relationship between the evaluation region 62 and region SXa is included in the master data NI, the evaluation region 62 may be present at a location separated from the region SXa as illustrated in FIG. 5. An inspection procedure in this case is described later. For convenience of description in the following description, the region SXa includes the evaluation region 62 as illustrated in FIG. 4. Furthermore, a center axis CL of the hole portion 61 is parallel to the W axis, and the evaluation region 6 is present on an extension line thereof.

Next, a summary of a method of identifying a position of a sliced plane in the region SXa is described, while referring to the master data M.

Figure 6A:
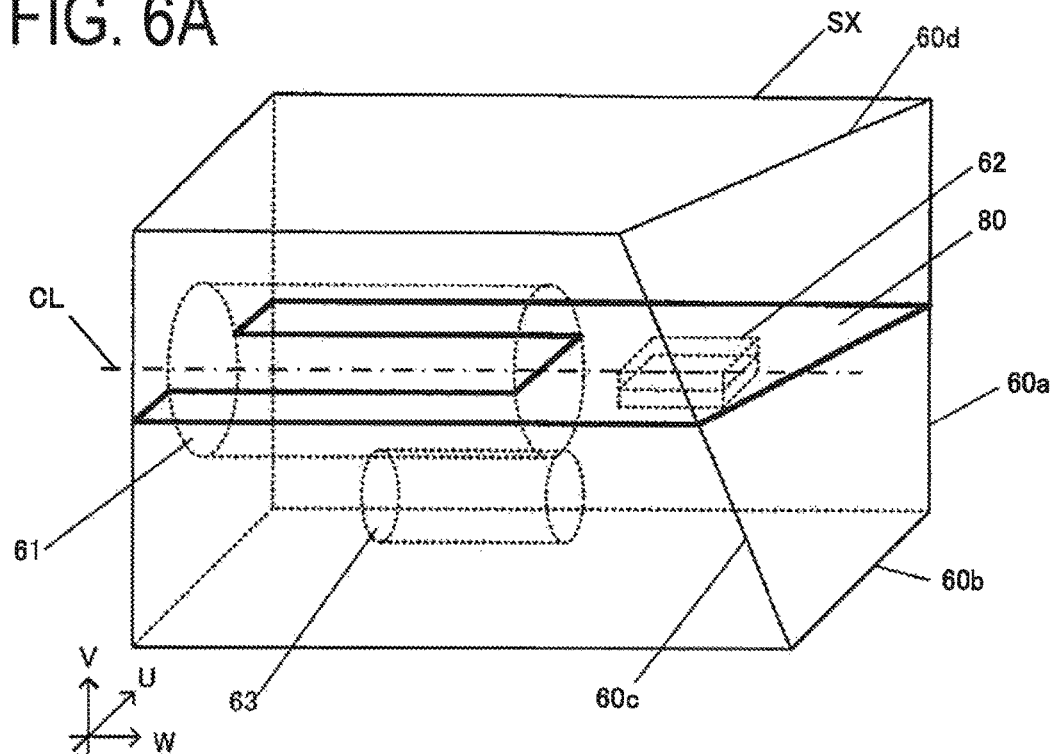
FIG. 6A is a conceptual diagram illustrating a relationship between a sliced plane and a reconstruction image.
Figure 6B:
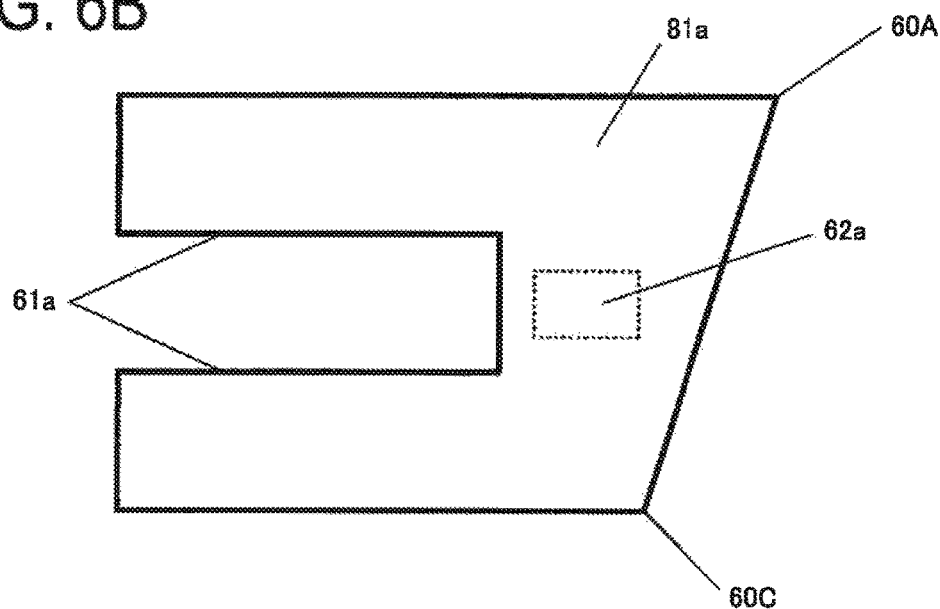
FIG. 6B is a conceptual diagram illustrating sliced plane and reconstruction image.

In general, the shape of a sliced plane changes based on the position of a sliced plane in the specimen SX. For example, if a sliced plane 80 includes the center axis CL of the hole portion 61, and is parallel to a UW plane as illustrated in FIG. 6A, a reconstruction image 81a of the sliced plane 80 has a shape as illustrated in FIG. 6B. A dotted line denoted by reference numeral 62a in FIG. 6B represents the evaluation region 62 in the reconstruction image 81a.

Figure 7A:
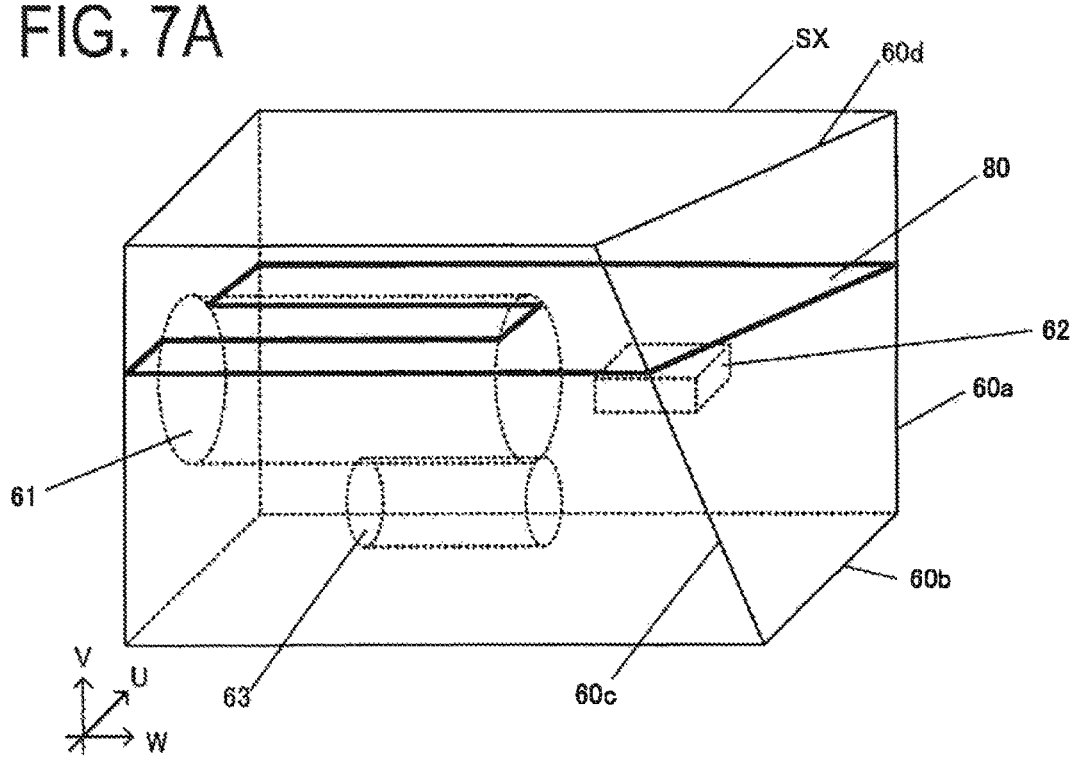
FIG. 7A is a conceptual diagram illustrating a relationship between a sliced plane and a reconstruction image.
Figure 7B:
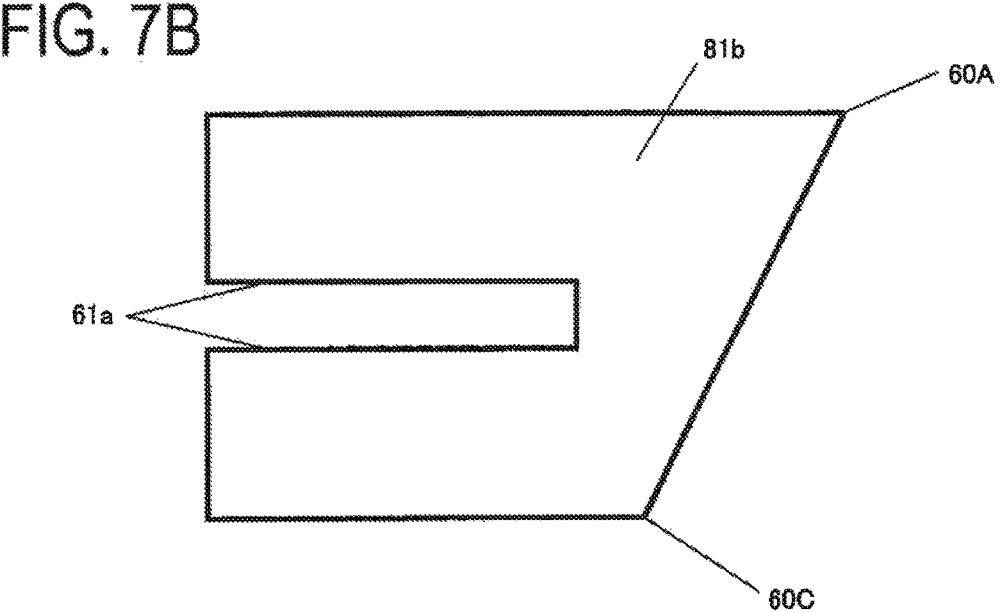
FIG. 7B is a conceptual diagram illustrating a sliced plane and reconstruction image.
Figure 8A:
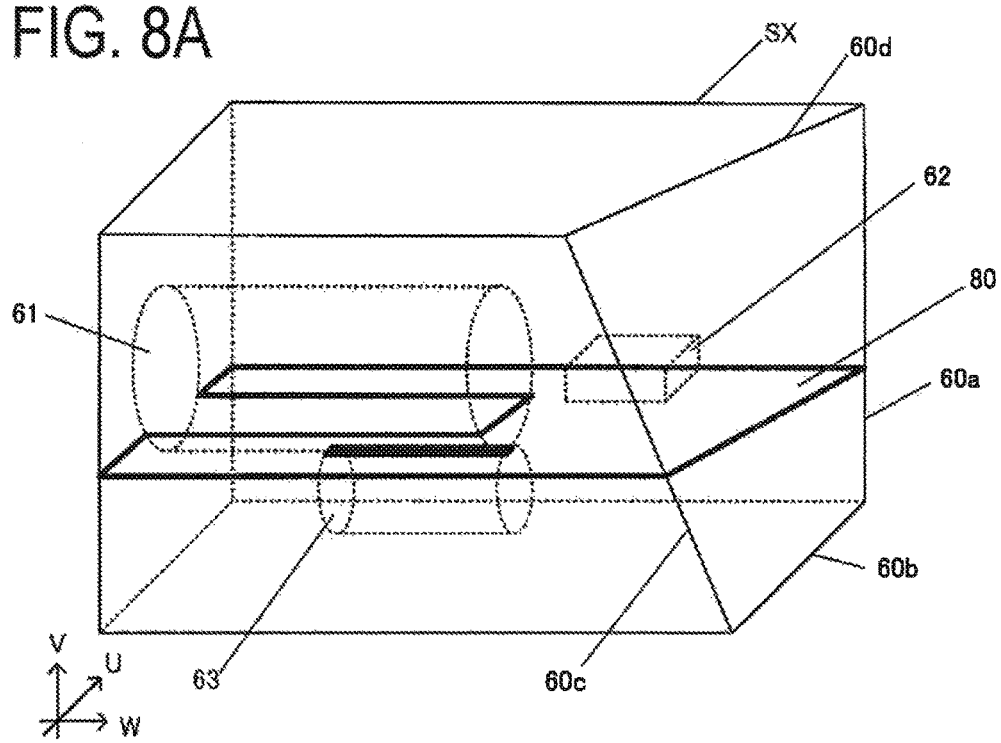
FIG. 8A is a conceptual diagram illustrating a relationship between a sliced plane and a reconstruction image.
Figure 8B:
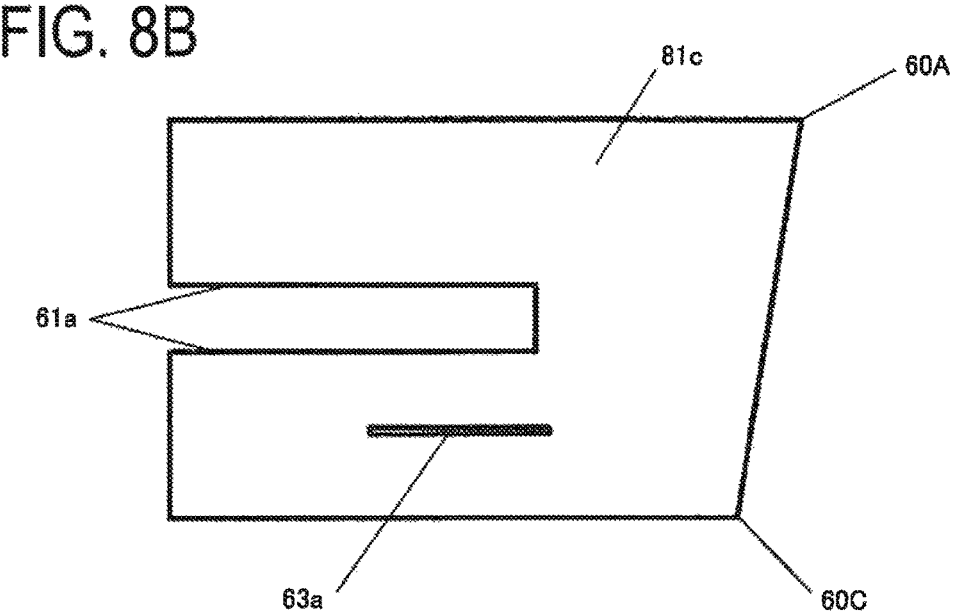
FIG. 8B is a conceptual diagram illustrating a sliced plane and reconstruction image.

Next, FIG. 7A illustrates a case where the sliced plane 80 is separated in the V axis+ direction as compared to the case in FIG. 6A. In this case, a reconstruction image 81b of the sliced plane 80 has the shape as illustrated in FIG. 7B. Furthermore, FIG. 8B illustrates a case where the sliced plane 80 is separated in the V axis– direction as compared to the case in FIG. 6A. In this case, a reconstruction image 81c of the sliced plane 80 has the shape as illustrated in FIG. 8B. As illustrated in FIG. 8A, the sliced plane 80 overlaps with an upper end portion in the drawing which is a part of the cast member 63. Therefore, a portion 63a with different brightness appears in the reconstruction image 81c illustrated in FIG. 8B.

Figure 9A:
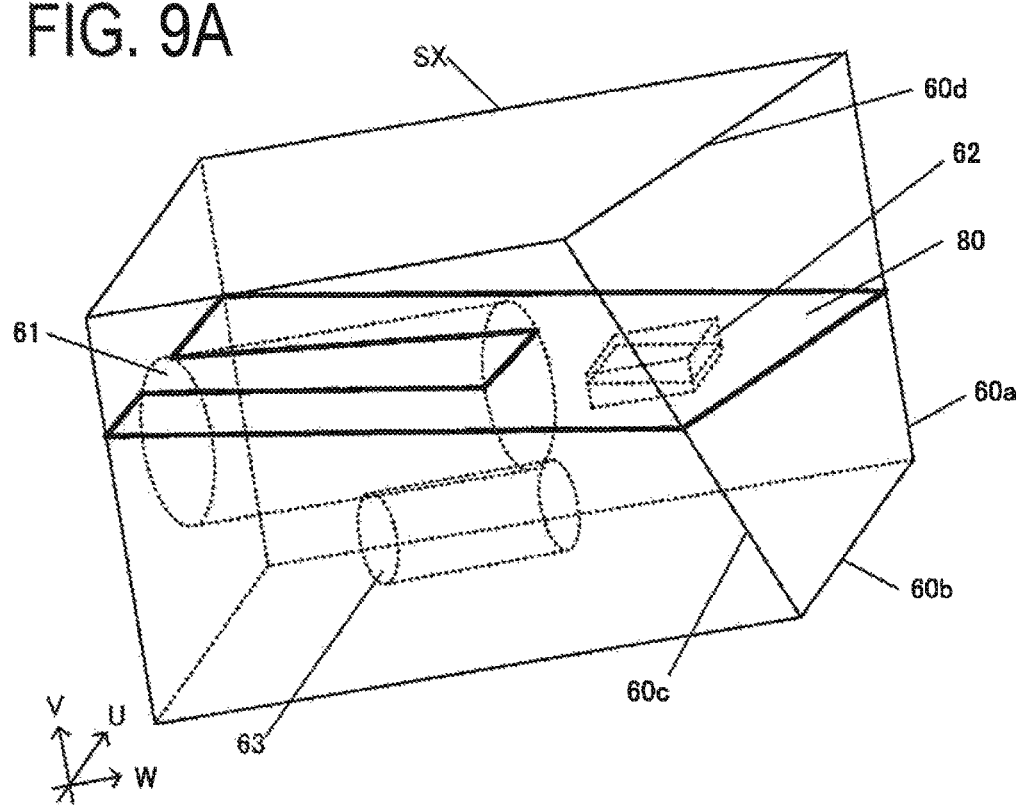
FIG. 9A is a conceptual diagram illustrating a relationship between a sliced plane and a reconstruction image.
Figure 9B:
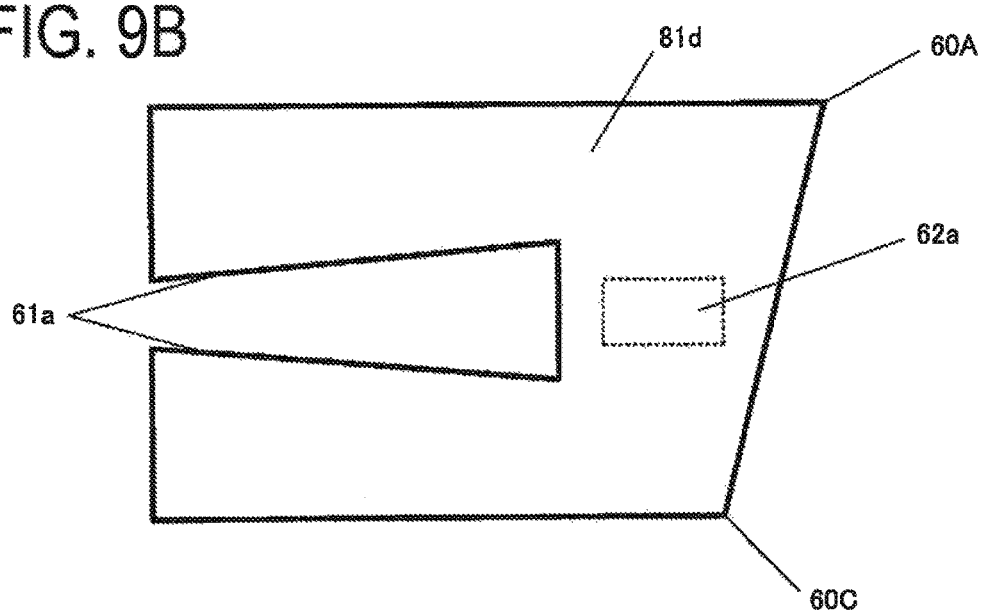
FIG. 9B is a conceptual diagram illustrating a sliced plane and reconstruction image.
Figure 10:
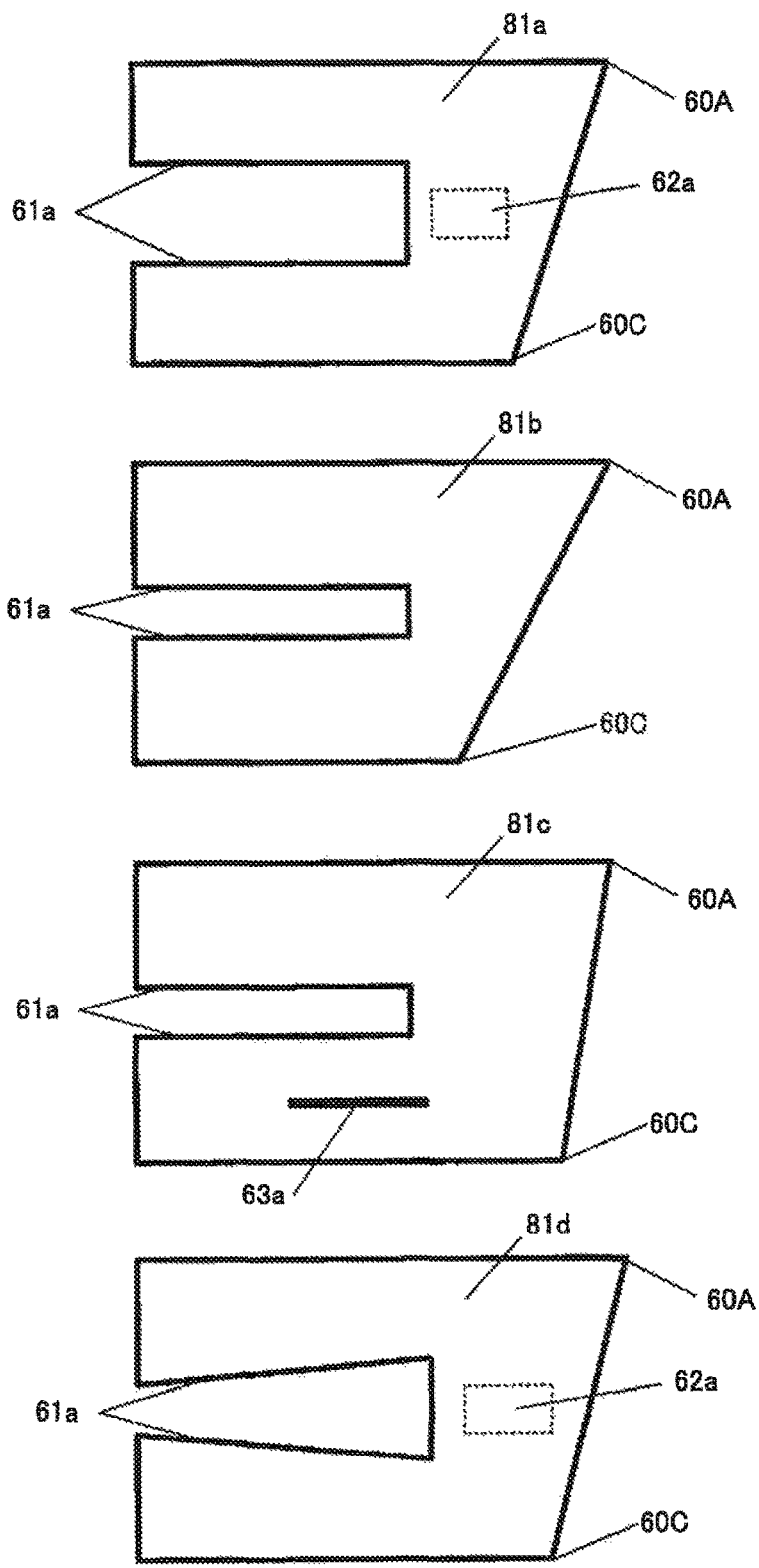
FIG. 10 is a conceptual diagram illustrating a reconstruction image corresponding to a different sliced plane.

Furthermore, FIG. 9A illustrates a case where the sliced plane 80 is not parallel to the UW plane. In this case, a reconstruction image 81d of the sliced plane 80 has the same shape as illustrated in FIG. 9B. FIG. 10 is a diagram illustrating the reconstruction images 81a to 81d side-by-side for comparison.

In the reconstruction image 81a, two lines 61a corresponding to an inner circumferential surface of the hole portion 61 are parallel. In the reconstruction image 81b, two lines 61a corresponding to an inner circumferential surface of the hole portion 61 are parallel, but the distance between both is shorter than the distance between the two lines 61a in the reconstruction image 81a. Furthermore, a position of an intersection 60C between the side 60c and the sliced plane 80 moves to a left side in the drawing as compared to an intersection 60C of the reconstruction image 81a.

In the reconstruction image 81c, two lines 61a expressing an inner circumferential surface of the hole portion 61 are parallel, but the distance between both is shorter than the distance between the two lines 61a in the reconstruction image 81a. Furthermore, a position of an intersection 60C between the side 60c and the sliced plane 80 moves to a right side in the drawing as compared to an intersection 60C of the reconstruction image 81a. As described above, a portion 63a with a different brightness, corresponding to a part of the cast member 63 appears in the reconstruction image 81c.

In the reconstruction image 81d, two lines 61a expressing an inner circumferential surface of the hole portion 61 are not parallel. Note that the two lines 61a of the reconstruction image 81 in FIG. 9B and FIG. 10 are simplified and expressed as a straight line, but are actually curved lines.

Therefore, the shape of the reconstruction image changes based on the position of the sliced plane 80 in the specimen SX. Therefore, by comparing the master data M with the shape of the sliced plane 80, the position of the sliced plane 80 in the region SXa corresponding to the master data M can be identified.

When specifically described, the two lines 61a are parallel in the reconstruction image 81a, and the sliced plane 80 is seen to be a surface including the center axis CL of the hole portion 61 from the distance between both lines (refer to FIG. 6A). Furthermore, the inclination of the sliced plane 80 can be known based on outline information, for example, the position of an intersection 60C or intersection 60A between the side 60a and the sliced plane 80, or the like. In this case, the sliced plane 80 is parallel with the W axis.

Furthermore, in the reconstruction image 81b and reconstruction image 81c, the distance between the center axis CL of the hole portion 61 and the sliced plane 80 in the Y direction is known based on the distance between the two lines 61a (refer to FIGS. 7A and 8A). Furthermore, the inclination and position of the sliced plane 80 can be known based on outline information, for example, the position of the intersection 60A, intersection 60C, or the like.

Furthermore, in the reconstruction image 81*d*, the two lines 61*a* are not parallel, and the distance between both increases in the W axis+ direction (refer to FIG. 9A). Therefrom, the sliced plane 80 is seen to be inclined. Furthermore, the inclination and position of the sliced plane 80 can be known by determining the positional relationship between the intersection 60A and intersection 60C.

As described above, the position of the sliced plane 80 in the specimen SX can be known by comparing outline information obtained from information of the sliced plane 80 with the information of the master data M. Furthermore, since the absorption rate of X-rays is different from peripheral material as illustrated by 63*a*, and therefore, the position of the sliced plane 80 in the specimen SX can be known by comparing the presence of a region with a different brightness in the reconstruction image, or shape thereof with the information of the master data M.

Figure 11A:
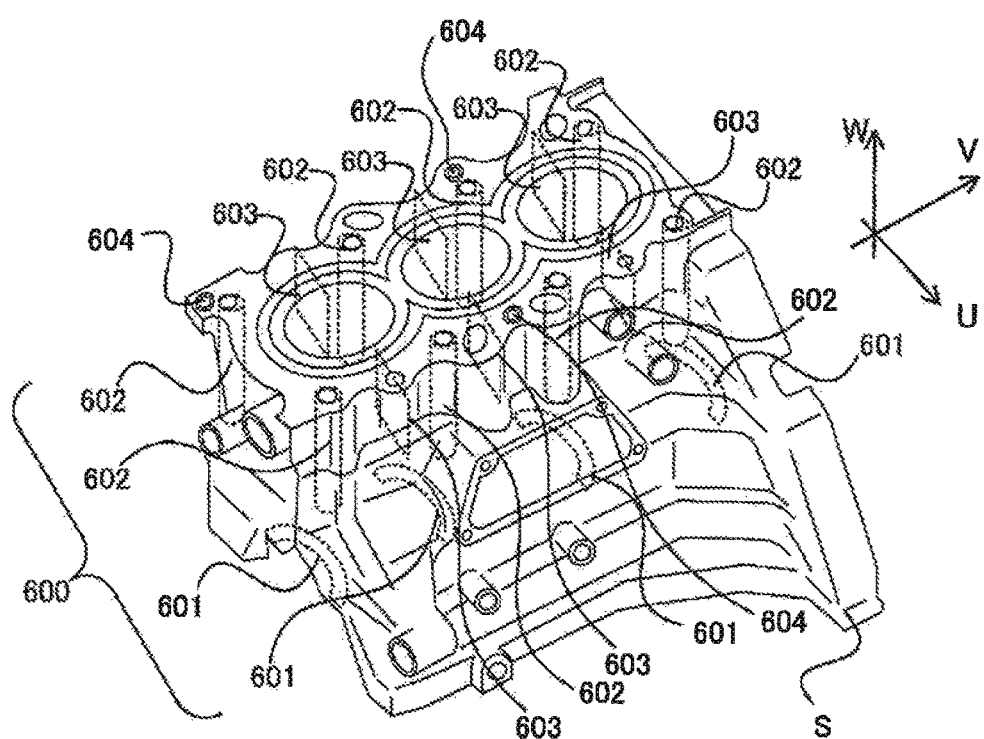
FIG. 11A is a diagram illustrating an example an evaluation region set if a cylinder block of an engine is inspected as a specimen.

For convenience of description, a structure of the specimen S is simplified in the above description. However, the actual specimen S often has a complex shape. For example, a case where a cylinder block of an engine having a complex shape as illustrated in FIG. 11A is described next. FIG. 11A is a perspective view of a cylinder block. The evaluation region 600 of the cylinder block is illustrated in FIG. 11A. Various three-dimensional shapes are included in the evaluation region 600. Examples include an evaluation region 601 near a crankshaft journal part, an evaluation region 602 near a cast pull pin, an evaluation region 603 near a cylinder part, and the like. Although not illustrated in FIG. 11A, a portion where generation of a shrinkage cavity is predicted in a simulation is also an evaluation region.

A surface on a right end in FIG. 11A of the cylinder block illustrated in FIG. 11A is placed on the placement stage 30 of the X-ray inspection device 100 as a placement surface, and a reconstruction image obtained by performing X-ray inspection for a plurality of sliced planes while gradually changing a sliced position is schematically illustrated in FIGS. 12A to 12E. For example, cross sections 83 and 84 of a recessed portion corresponding to a cast pull pin, a cross section 85 of a cooling channel, a cross section 86 of a cast iron portion cast in a crankshaft journal part, a cross section 87 inside a crank case, a cast iron liner portion 88 cast in a cylinder liner part, and the like are expressed in reconstruction images 82*a* to 82*e* respectively illustrated in FIGS. 12A to 12E. Note in FIG. 12, evaluation region 62*a* is set only in FIG. 12C.

As illustrated in FIGS 12A to 12E, when the sliced position in the cylinder block is changed, the reconstruction images are seen to change. In other words, in FIG. 11A, a surface parallel to the WU plane is placed on the placement stage 30, and in FIG. 11A, an end surface in the V axis+ direction is placed on the placement stage 30. For example, in the cylinder block, an outline structure and internal structure are complex, and therefore, in the cylinder block, the outer structure and internal structure of the WU plane is different based on a position in the V direction, for example. The cross section 83 resulting from the shape of the recessed portion is confirmed in FIG. 12A, FIG. 12B, and FIG. 12C, but cannot be confirmed in FIG. 12D and FIG. 12E. Furthermore, when comparing FIG. 12B and FIG. 12C, the surface areas surrounded by a cross section of the recessed portion are different. This shows that a surface area of the recessed portion in the WU plane of FIG. 12B decreases toward FIG. 12C based on movement along the V axis. Therefore, the outline structure of a specimen is not uniform along the V direction. Therefore, there is a difference depending on the structure of the specimen and detected position. Therefore, the position in the V direction can be identified by using a size of a surface area surrounded by the recessed portion 83, for example. For example, even with an image in which a reconstruction image is prepared by measuring a specimen different from FIG. 12C, a measurement position in the V direction of the different specimen can be estimated by using the surface area surrounded by the recessed portion 83 as an index. Therefore, if the structure changes around the measurement position, a cross-sectional structure thereof may be used and compared with the master data M. In this case, it is possible to use only this structure for comparison, and therefore, a relative position can be determined in a shorter amount of time. Furthermore, in the subject for example, a portion of the internal structure of the subject may break during manufacturing in some cases. Therefore, when comparing with the master data M based on the shape of the subject, shape data does not match due to breaking of the internal structure, and thus searching for a position of a measurement data from the master data M is difficult. In this case, correlation failure with the master data M may be suppressed by weighting a partial shape of a tomographic image. Furthermore, when it is known that a cavity can be formed in the material of the internal structure of the subject during manufacturing, the outline of the material thereof may be increased in weight more than in the material to determine the correlation thereof. Thereby, correlation failure with the master data M can be suppressed. Of course, a plurality of points may be used for weighting, rather than just one point.

Furthermore, the material used in the cylinder block is not limited to one type. For example, in FIG. 12A to FIG. 12E the material used is different from other portions at the cast iron portion 86. For example, in the present embodiment, the material used in the cast iron portion 86 has different elements from material used in the periphery thereof. Of course, as an example of material used in 86, when an alloy is used, the composition ratio for generating the alloy may be different from the periphery thereof. Therefore, the absorption rate of X-rays by the periphery and the cast iron portion 86 is different, and therefore, the image obtained by reconstituting displays a luminosity that is different from the periphery thereof. Therefore, when comparing with the master data M, the position during measurements may be estimated using luminosity information of the image.

Furthermore, for example, the cast iron liner portion 88 cast in the cylinder liner part is not recognized in the reconstruction images 82*a* to 82*d*, but is clearly expressed as a portion with high luminosity in the reconstruction image 82*e*. Furthermore, for an outline of a cylinder block other than the aforementioned, various changes are seen based on changing the sliced position.

As described above, when the sliced position is changed, a change appears in relation to the luminosity or outline of the reconstruction image, and therefore, the information can be compared with the master data M to know the position of the sliced plane 80 in the specimen SX. Thereby, a reconstruction image of a sliced plane to be used in evaluation region inspection is selected.

Figure 13A:
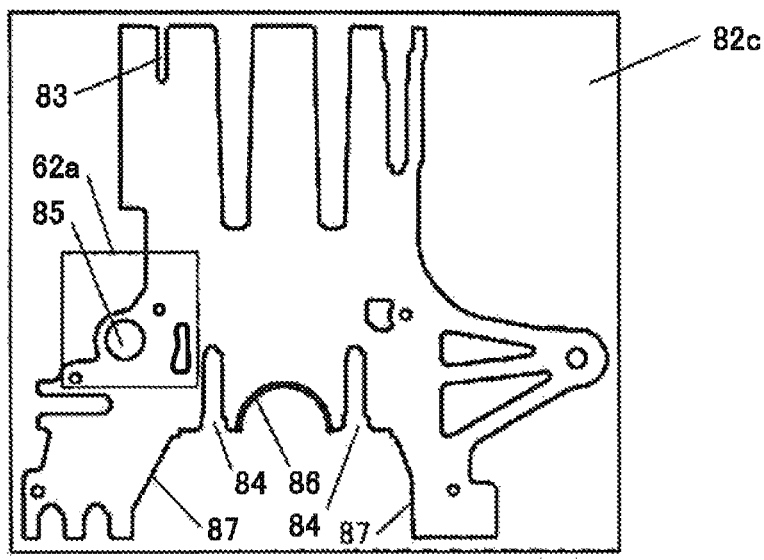
FIG. 13A illustrates a reconstruction image selected as a reconstruction image of a sliced plane to be used in inspecting an evaluation region.
Figure 13B:
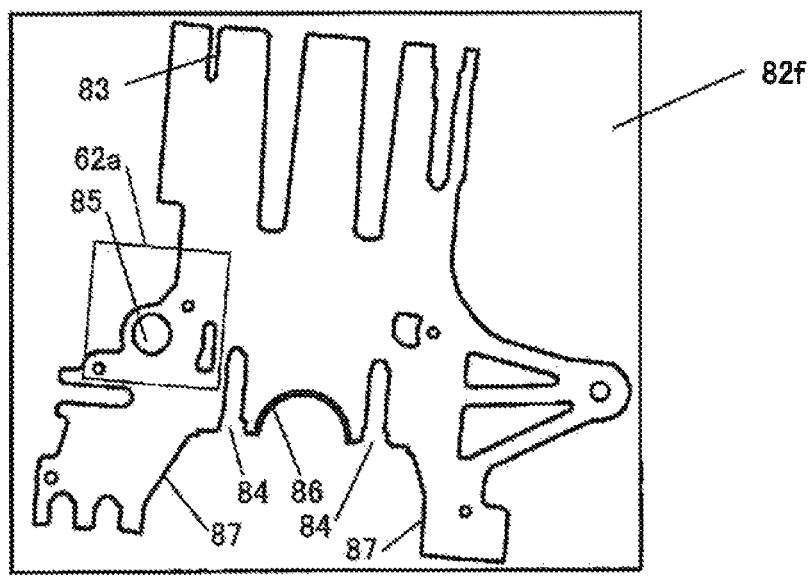
FIG. 13B illustrates a reconstruction image if a rotation is calculated with regard to data corresponding to the master data.

FIG. 13A illustrates a selected reconstruction image. Herein, the image is the same as the reconstruction image 82*c* in FIG. 12C. Next, calculation is performed on whether or not the reconstruction image to be used in evaluation region inspection is rotated and/or misaligned with regard to data corresponding to the master data M, by comparing with master data M information. For example, in FIG. 13B, a structure in an obtained reconstruction image 82*f* deviated based on different conditions where the subject was placed, as compared to when the master data M was acquired. In FIG. 13B, the structure rotates. In this case, when a correlation with the master data M is acquired, a correlation failure occurs, and estimating the target structure in the master data M is difficult. Therefore, in this case, the rotation amount and misalignment amount of FIG. 13B with regard to FIG. 13A can be determined using a shape of a region surrounded by reference number 62a in FIG. 13A and FIG. 13B. In this case, when a position in the V direction changes as in FIG. 12A to FIG. 12E for example, a location with a different cross-sectional shape thereof is not preferred. Furthermore, the region 62a is set in advance in FIGS. 13A and 13B, but if the region 62a is not set, in a cross-sectional image obtained by reconstructing, a circular image, with a predetermined size is extract from the acquired image, and a position of a circle corresponding 85 is extracted from the circular image. In this case, an image in a predetermined region of a periphery of the circle is selected, and rotational deviation and positional deviation in selected regions may be determined. Note that the surface of the region 62a may be the same or different in FIG. 13A and FIG. 13B. Note that for comparison with the master data, voxel data of the obtained reconstruction image may be mutually compared, or the voxel data may be compared after converting to a two-dimensional image.

The master data M may be information based on an outline shape of the specimen S obtained by another inspection device other than the X-ray inspection device 100, as with a three-dimensional measurement device, for example. Alternatively, the data may be design information of the specimen S, as with CAD data of-the specimen S. Furthermore, the master data M may be measurement information of the specimen S obtained by inspecting a part or all of the specimen S using the X-ray inspection device 100. Several cases are described next.

(1) If the Master Data M is Information Based on an Outline Shape of the Specimen S Obtained by an Inspection Device other than the X-Ray Inspection Device 100

Figure 2:
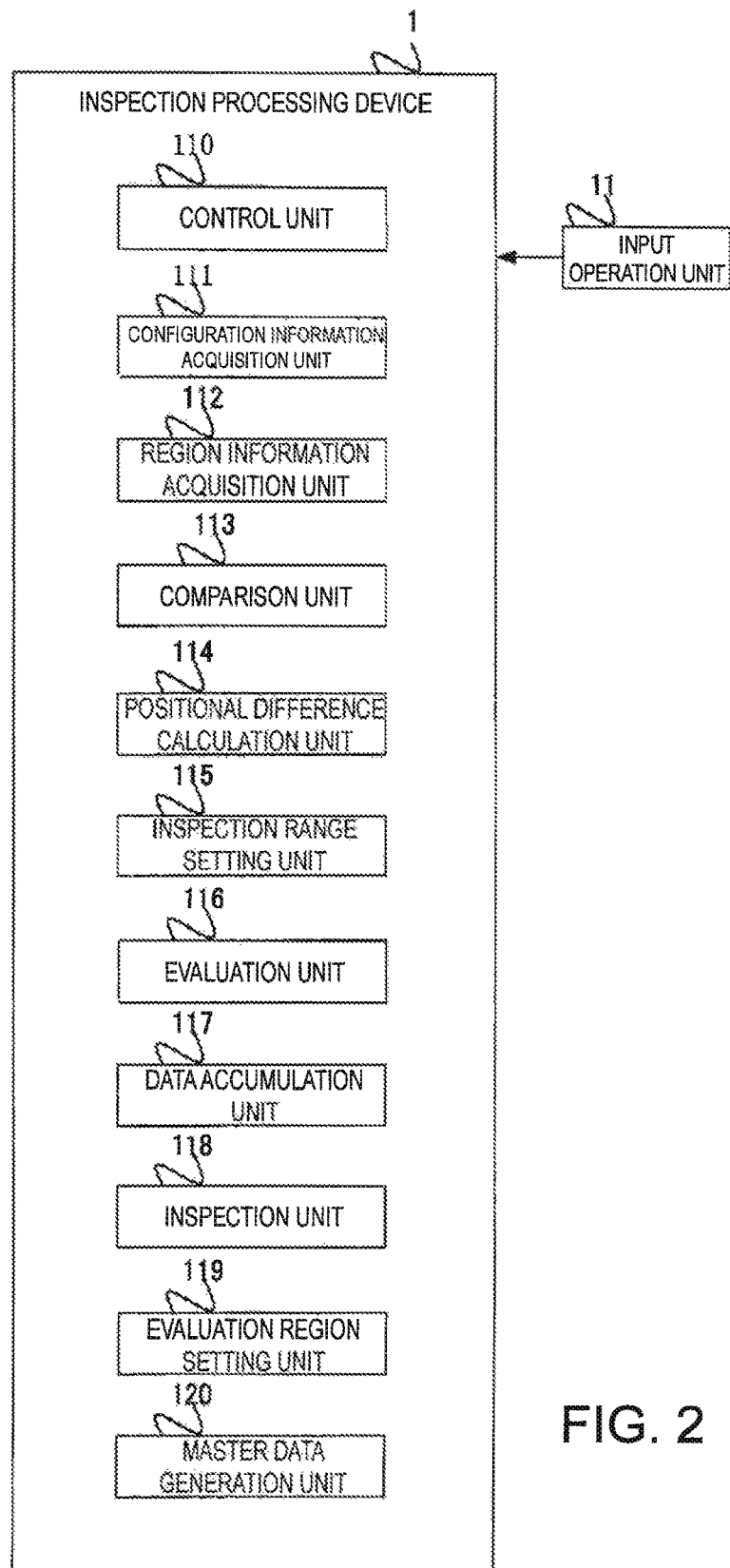
FIG. 2 is a block diagram of an inspection processing device.

The configuration information acquisition unit 111 illustrated in FIG. 2 acquires outline information of at least a part of the specimen S from another inspection device. The master data generation unit 120 generates master data M based on outline shape information of the specimen S acquired by the configuration information acquisition unit 111, information expressing a correlation between a part corresponding to the outline shape and a position in the specimen S, and information expressing a correlation between a position of an evaluation region and a position in the specimen S, for example. The master data M generated by the master data generation unit 120 is stored in the data accumulation unit 117.

(2) If the Master Data M is Based on Design Information of the Specimen S

The configuration information acquisition unit 111 illustrated in FIG. 2 acquires information input manually by an operator based on design information such as three-dimensional CAD or the like. The master data generation unit 120 generates master data M based on design information of at least a part of the specimen. S acquired by the configuration information acquisition unit 111, information expressing a correlation between a position corresponding to the design information and a position in the specimen S, and information expressing a correlation between a position of the evaluation region and a position in the specimen S. The master data M generated by the master data generation unit 120 is stored in the data accumulation unit 117. Note that when the master data M is generated based on design information, a region with low solidification shrinkage is predetermined from regions where a removing process is not performed, based on a simulation of a casting process, actual measurement value of the specimen S, or the like, and the master data M is preferably generated based on design information of the region. The configuration information acquisition unit 111 may automatically acquire design information such as three-dimensional CAD or the like through an interface.

(3) If the Master Data M is Based on Measurement Information according to the X-ray Inspection Device 100

The X-ray inspection device 100 generates master data M as follows.

In the present embodiment, if a plurality of the specimens S are sequentially inspected by the X-ray inspection device 100, the master data M is generated from measurement information of an initially inspected specimen S among the plurality of specimens S. The plurality of specimens S are products manufactured based on the same design information. Therefore, whether or not the plurality of specimens S are all manufactured according to the design information is inspected, for example.

First, the initially inspected specimen S is placed on the placement stage 30. In descriptions hereinafter, the initially inspected specimen S is referred to as an initial specimen S1. A positioning pin not illustrated in the drawing is provided on the placement stage 30, and the initial specimen S1 is brought into contact with the positioning pin, and therefore, the initial specimen S1 can be positioned on the placement stage 30. Note that the positioning pin is not required to be provided on the placement stage 30.

When the initial specimen S1 is placed on the placement stage 30, an upper surface of the placement stage 30 is made parallel with the XZ plane. In this condition, the partial scan is performed while rotating the placement stage 30. As described later, for specimens S sequentially inspected after the initial specimen S1, the height or inclination angle of the placement stage 30 is adjusted such that essentially the same position as the partial scan on the initial specimen S1 is performed.

The inspection range setting unit 115 illustrated in FIG. 2 sets a thickness where a partial scan region in the initial specimen S 1 includes an inspection target region and .has redundancy in the Y direction as described. above. Note that variation information expressing variations in a type of specimens S or outline dimensions of the specimens S is stored in the data accumulation unit 117, and the inspection range setting unit 115 may set the thickness of the partial scan region of the initial specimen S1 based on the variation information. The partial scan region of the initial specimen S1 set thereby is referred to as a master data region. The master data region is a region corresponding to the region SXa illustrated in FIG. 4, for example.

The movement control unit 52 controls the manipulator unit 36, and the partial scans are performed on the master data region while rotational driving and moving the placement stage 30 in the Y direction, such that a transmission image for generating a reconstruction image in the master data region set by the inspection range setting unit 115 can be acquired. The inspection unit 118 generates internal information of the master data region based on partial scan data.

The master data generation unit 120 adds information related to the evaluation region or information expressing to which part of the initial specimen S1 the master data region corresponds, to internal information of the master data region, and generates the master data M.

Note that information related to an evaluation region stored in the data accumulation unit 117 set by the evaluation region setting unit 119 can be used as the information related to the evaluation region. Furthermore, information expressing to which part of the initial specimen S1 the master data region corresponds is obtained as follows, for example. First, a reconstruction image in an arbitrary sliced plane is generated from internal information of the master data region, and the position of the arbitrary sliced plane in the initial specimen S1 is identified by comparing with design information of the initial specimen S1. If the part of the initial specimen S1 to which the position of the arbitrary sliced plane corresponds can be identified, the part of the initial specimen S1 to which the master data region corresponds can also be identified.

Thereby, the master data M generated by the master data generation unit 120 is stored in the data accumulation unit 117.

Figure 14:
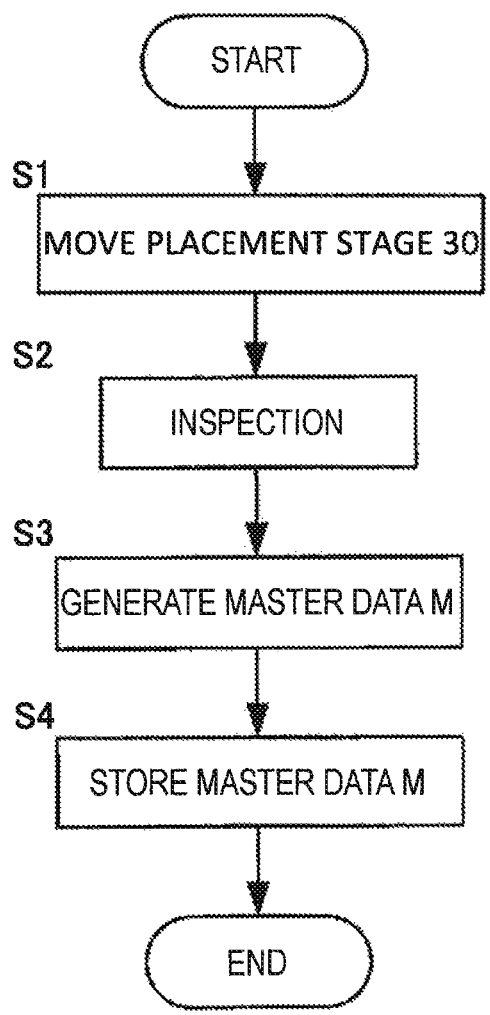
FIG. 14 is a flowchart describing a process of generating master data from measurement information of an initial specimen.

A process of generating the master data M from measurement information of the initial specimen S1, while referring to the flowchart of FIG. 14. A program for executing processes shown in the flowchart of FIG. 14 is stored in advance in a memory (not illustrated in the drawing), and is read and executed by a microprocessor of the inspection processing device 1. Note that the initial specimen S1 is placed on the placement stage 30.

In step S1, the control unit 110 instructs the movement control unit 52 to control the manipulator unit 36 to move the placement stage 30 at an inspection start position for acquiring the master data M, and then proceeds to step S2. In step S2, the control unit 110 instructs the X-ray control unit 51 to control the X-ray source 2. The controller unit 110 instructs the movement control unit 52 to control the manipulator unit 36 and perform rotation of the placement stage 30 and movement in the Y direction. The inspection unit 118 performs inspection while the placement stage 30 moves a distance corresponding to a thickness set by the inspection range setting unit 115. Thereby, the internal information of the master data region is acquired.

After step S2 is executed, the process proceeds to step S3. In step S3, the master data generation unit 120 adds information related to the evaluation region or information expressing to which part of the initial specimen S1 the master data region corresponds, to internal information of the master data region acquired in step S2, and generates the master data M. When step S3 is executed, the process proceeds to step S4. In step S4, the master data generation unit 120 stores the master data M generated in step S3 in the data accumulation unit 117, and then completes the program.

—Inspection Process—

Using the master data M of any of the aforementioned (1) to (3), the X-ray inspection device 100 sequentially inspects the plurality of specimens S as follows.

First, the specimen S is placed on the placement stage 30. As described above, the specimen S is brought into contact with a positioning pin of the placement stage 30, and therefore, the specimen S can be positioned on the placement stage 30. Note that when the specimen S is placed, the upper surface of the placement stage 30 is made parallel with the XZ plane.

The inspection range setting unit 115 sets a partial scan region of the specimen S in a region including the inspection target region. The inspection target region is a region selected as a region to be inspected from a plurality of evaluation regions per inspection process.

Note that the inspection time increases as the thickness of the partial scan region increases, and therefore, the thickness of the partial scan region is preferably as thin as possible. Therefore, the thickness of the partial scan region set in this case is generally thinner than a thickness of the master data region which is the partial scan region of the initial specimen S1. The partial scan region set by the inspection range setting unit 115 is referred to as a target partial scan region.

Next, the partial scan of the specimen S is performed. The partial scan on the partial scan region with reduced thickness set when sequentially inspecting the specimens S is referred to as a thin sliced scan. The movement control unit 52 controls the manipulator unit 36 to rotationally drive and move the placement stage 30 in the Y direction. The region information acquisition unit 112 acquires region information obtained by the thin sliced scan.

The comparison unit 113 compares the region information acquired by the region information acquisition unit 112 based on the thin sliced scan with the master data M stored in the data accumulation unit 117, and determines, based on the results, whether or not the thin sliced scan region corresponds to the inspection target region set by the inspection range setting unit 115, in other words, whether or not the thin sliced scan region includes the inspection target region set by the inspection range setting unit 115. For example, the comparison unit 113 calculates a correlation coefficient between a cross-sectional shape of the inspection target region determined from the master data M and region information based on the thin sliced scan, and then makes a determination based on the value of the correlation coefficient. Note that when calculating the correlation coefficient, in order to not be affected by an accidental image change caused by a cavity occurring which is an internal defect of the specimen S, a cast pull pin of a metal mold breaking, or the like, a region where these may occur may be removed from the calculation, or the weighting may be reduced.

If the comparison unit 113 determined that the thin sliced scan region includes the inspection target region set by the inspection range setting unit 115, the evaluation unit 116 evaluates the quality of the specimen S based on the region information obtained by the thin sliced scan. Thereafter, inspection of the subsequent specimen S is initiated.

If the comparison unit 113 determined that the thin sliced scan region does not include the inspection target region, the positional difference calculation unit 114 calculates the difference (deviation) between a position of the inspection target region and position in the specimen S corresponding to region information acquired by the thin sliced scan, based on comparison results according to the comparison unit 113. Thereby, based on the characteristics of the reconstruction image obtained by the thin sliced scan, it can be known which part of the master data region corresponds to a part where the thin slice scan is performed. Herein, examples of a characteristic Shape expressed in each portion of the reconstruction image include a position of the intersection 60A or intersection 60C, direction of the line 61A, appearance of the portion 63a with a different brightness than the periphery, and the like, in the reconstruction images 81a to 81d illustrated in FIG. 10.

The movement control unit 52 controls the manipulator unit 36 to move the placement stage 30 such that the difference between positions of the thin sliced scan region and inspection target region, calculated by the positional difference calculation unit 114, is zero.

Next, a thin sliced scan is performed again for the specimen S. The position of the specimen S is corrected such that a position of a re-performed thin sliced scan (hereinafter, referred to as rescan) includes the position of the inspection target region. Therefore, a region of the re-performed thin sliced scan is performed for the inspection target region. The region information acquisition unit 112 acquires region information obtained by the rescan.

The comparison unit 113 compares region information, based on the rescan, acquired by the region information acquisition unit 112 with master data M stored in the data accumulation unit 117, and based on the results, determines whether or not the scan region when rescanning includes the inspection target region set by the inspection range setting unit 115. If the comparison unit 113 determined that the rescan region includes the inspection target region set by the inspection range setting unit 115, the evaluation unit 116 evaluates the quality of the specimen S based on the region information obtained by the rescan.

If the comparison unit 113 determined that the rescan region does not include the inspection target region, the positional difference calculation unit 114 calculates the difference between the position of the inspection target region and the position in the specimen S corresponding to region information acquired by the rescan, based on comparison results according to the comparison unit 113, and then repeats the same process below. However, the position of the specimen S is corrected such that the rescan region includes the inspection target region, and therefore, after the position of the specimen S is corrected, the rescan position has a high possibility of including the inspection target region. Thereafter, inspection of the subsequent specimen S is initiated.

Note that whether or not the scan region of the thin sliced scan or rescan includes the inspection target region may be determined based on whether or not the entire inspection target region is included in the scan region of the thin sliced scan or rescan, or may be determined based on whether or not a part of the inspection target region is included in the scan region of the thin sliced scan or rescan. The degree at which the inspection target region is included in the scan region of the thin sliced scan or rescan is preferably appropriately set based on the objective of the inspection.

Furthermore, determination of whether or not the scan region of the thin sliced scan or rescan includes the inspection target region may determine whether or not the positional difference between the target partial scan region and the scan region of thin sliced or rescan is exactly zero, or may be performed based on determining whether or not the difference between both is within a predetermined range, for example. The degree of the predetermined difference is preferably appropriately set based on the objective of the inspection.

Figure 15:
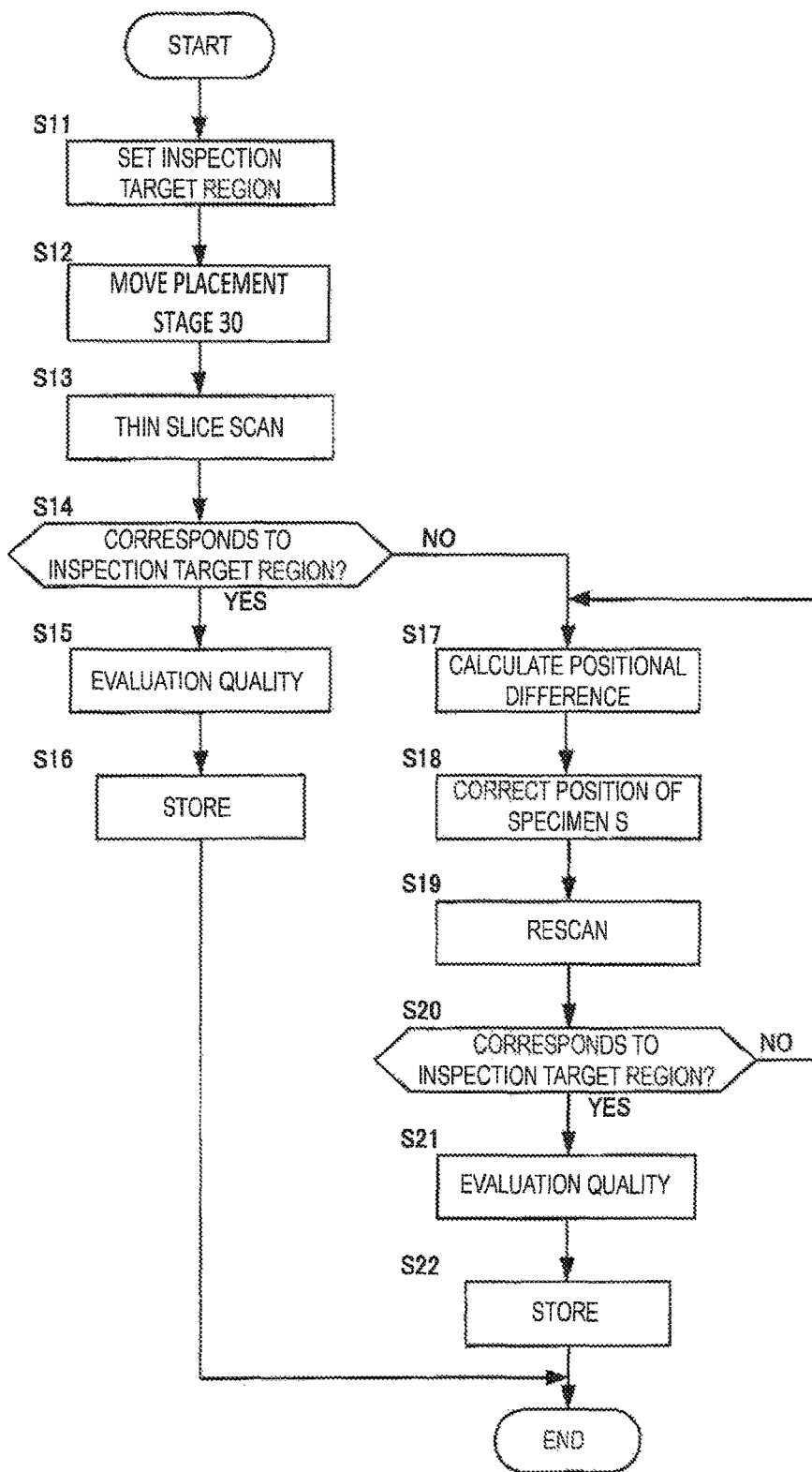
FIG. 15 is a flowchart describing an inspection process of the first embodiment.

A measurement process of the specimen S in the present embodiment will be described while referring to the flowchart in FIG. 15. A program for executing processes shown in the flowchart of FIG. 15 is stored in advance in a memory (not illustrated in the drawing), and is read and executed by a microprocessor of the inspection processing device 1. Note that the specimen S is placed on the placement stage 30.

In step S11, the inspection range setting unit 115 sets a target partial scan region, and the proceeds to step S12. In step S12, the control unit 110 instructs the movement control unit 52 to control the manipulator unit 36 to move the placement stage 30 to a thin sliced scan movement start position, and then proceeds to step S13. In step S13, the control unit 110 instructs the X-ray control unit 51 to control the X-ray source 2. The controller unit 110 instructs the movement control unit 52 to control the manipulator unit 36 to set the sliced plane, and rotate and move the placement stage 30 in the Y direction. Thereby, a thin sliced scan is performed. The inspection unit 118 generates internal information based on the thin sliced scan data, and then proceeds to step S14.

In step S14, the comparison unit 113 compares region information acquired based on the thin sliced scan with master data M stored in the data accumulation unit 117, and determines whether or not the thin sliced scan region includes the target inspection region.

If determined to be affirmative in step S14, the process proceeds to step S15, and then the evaluation unit 116 evaluates the quality of the specimen S based on the region information obtained by the thin sliced scan, and then proceeds to step S16. In step S16, the data accumulation unit 117 stores information based on the thin sliced scan, information related to the positional relationship between the thin sliced scan region and the target inspection region, and information related to evaluation results of the quality of the specimen S, and then completes the program.

If determined to be negative in step S14, the process proceeds to step S17, and then the positional difference calculation unit 114 calculates the positional difference between the thin sliced scan position and the inspection target region position based on the comparison results by the comparison unit 113, and then proceeds to step S18.

In step S18, the control unit 110 instructs the movement control unit 52 to control the manipulator unit 36 to move the placement stage 30 such that the positional difference between the positions of the thin sliced scan region and the inspection target region is zero, so as to offset the positional difference calculated in step S18, and then proceeds to step S19.

In step S19, the control unit 110 instructs the X-ray control unit 51 to control the X-ray source 2. The controller unit 110 instructs the movement control unit 52 to control the manipulator unit 36 to measure the sliced plane, and rotate and move the placement stage 30 in the Y direction. Thereby, a rescan is performed. The inspection unit 118 generates internal information based on rescan data, and then proceeds to step 20.

In step S20, the comparison unit 113 determines whether or not the rescan region includes the inspection target region. If determined to be affirmative in step S20, the process proceeds to step S21, and then the evaluation unit 116 evaluates the quality of the specimen S based on the region information obtained by the rescan, and then proceeds to step S22. In step S22, the data accumulation unit 117 stores information based on the thin sliced scan, information related to the positional relationship between the thin sliced scan region and the target inspection region, and information related to evaluation results of the quality of the specimen S, and then completes the program. If determined to be negative in step S20, the process proceeds to step S17.

—Evaluation of Quality of Specimen S—

Figure 16:
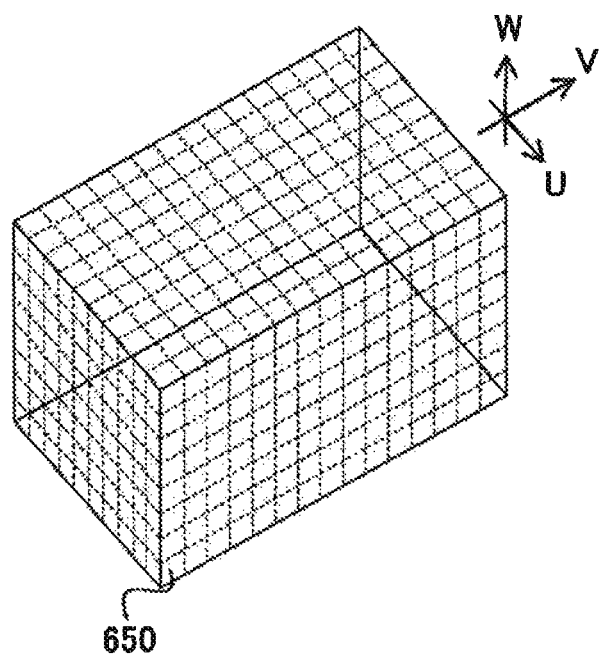
FIG. 16 is a diagram illustrating a lattice grid.

The evaluation unit 116 evaluates the quality of the specimen S based on the region information obtained by partially scanning the specimen S. As an example of an evaluation procedure, a lattice grid is formed dividing into unit three-dimensional lattices the inspection target region which is a part of the partial scan region, in other words, region including a region selected as the inspection target region from the plurality of evaluation regions. An example of a lattice grid 650 is illustrated in FIG. 16. The lattice grid 650 is three-dimensionally provided along the UVW direction of an orthogonal coordinate including the U axis, V axis, and W axis set with regard to the specimen S. The inspection target region is divided by a plurality of lattice grids 650, and therefore, when the inspection results of the specimen S is analyzed, the inspection results can be handled by the lattice grid 650. For example, the volume (volume ratio) of a cavity per volume of a unit lattice grid can be calculated, and the quality of the specimen S can be evaluated by the results.

In the present embodiment, the posture of the plurality of sequentially inspected specimens S is corrected as described above, and therefore, the position of the inspection target region with regard to the partial scan region is the same for each of the plurality of specimens S. Therefore, when the inspection target region of each of the plurality of specimens S is formed into a lattice grid, the dividing position and dividing direction of the lattice grid 650 can be matched between the inspection target regions. In other words, for the plurality of sequentially inspected specimens S, the individual lattice grids 650 can be set at the same position and the specimens can be inspected based thereon.

For example, a case of inspecting a cavity that is present inside the specimen S will be described. The evaluation unit 116 detects the presence or absence of the lattice grids 650, and calculates the volume ratio of a cavity in the lattice grid 650 when inspecting the cavity. Furthermore, the evaluation unit 116 calculates the thickness of the lattice grids 650. The evaluation unit 116 evaluates the quality of individual specimens S based on an index set in the lattice grids 650 based on the volume ratio and thickness of the calculated cavity.

In the aforementioned first embodiment, the following effects are achieved.

(1) The region information acquisition unit 112 acquires region information obtained by the partial scan. The comparison unit 113 determines whether or not the partial scan region corresponds to the inspection target region set by the inspection range setting unit 115, based on region information obtained by the partial scan and master data M stored in the data accumulation unit 117. Thereby, even with a partial scan, in other words, a scan of only a part of the specimen S, whether or not a region to be scanned is scannable can be determined, and whether or not the partial scan region is valid can be determined. Thereby, inspection of the specimen S can be performed accurately and in a short period of time, which contributes to improving productivity.

(2) The master data M includes information related to the shape of at least a part of the specimen S. By referring the partial scan region (thin sliced scan region or rescan region) to the master data M, the position in the master data region that the partial scan region corresponds to can he identified. Thereby, a deviation between the region to be scanned and region where the partial scan is actually performed is known, and therefore, when performing the partial scan again (rescan), the position of the specimen S can be corrected. Therefore, even if the specimen S deviates or inclines in the Y direction due to a variation in shape, essentially the same region for the plurality of specimens S can be scanned, and therefore, the number of rescans can be minimized. Thereby, the inspection time of the specimen S can be reduced, which contributes to improving productivity, (3) In consideration of shape variation of the specimen S, the thickness of the master data region is thicker than the thickness of the partial scan region. Thereby, even if the specimen S deviates or inclines in the Y direction due to a variation in shape, the region where the partial scan is performed is easy to verify with regard to the master data region. Thereby, the inspection time of the specimen S can be reduced, which contributes to improving productivity.

(4) The master data M can be generated using outline information of the specimen S obtained by an inspection device (such as a three-dimensional measurement machine) other than the X-ray inspection device 100. In this case, inspection of the specimen can be accurately performed even without design information of the specimen S.

(5) The master data M can be generated using design information (such as CAD information) of the specimen S. In this case, the master data M of the specimen S is not required to be generated by the X-ray inspection device 100 or other inspection device.

(6) The master data M can he generated using scan data obtained when performing inspection of the initial specimen S1 by the X-ray inspection device 100. In this case, the master data M can be generated simultaneously with the inspection, and therefore is efficient.

(7) When the thin sliced scan region is determined to correspond to the inspection target region, it is configured that the quality of the specimen S is evaluated based on region information of the thin sliced scan region. Furthermore, when the thin sliced scan region is determined not to correspond to the inspection target region, a positional deviation between the thin sliced scan region and. the inspection target region is calculated. Thereby, the posture of the specimen can be easily corrected, and therefore, the rescan region has a high possibility of including the inspection target region, which contributes to improving productivity.

(8) When the positional deviation between the thin sliced scan region and the inspection target region is calculated, the inspection unit 118 controls the manipulator unit 36 through the movement control unit 52 to move the placement stage 30, such that the positional deviation is zero. Thereby, the position of the specimen S is accurately corrected, and therefore, the rescan can be quickly initiated, which contributes to improving productivity.

—Second Embodiment—

An X-ray inspection device and an inspection processing device for an X-ray inspection device will be described according to a second embodiment of the present invention while referring to the drawings. In the following description, the same reference numeral will be attached to the same components as the first embodiment, and differing points will mainly be described. Points that are not particularly described are the same as the first embodiment.

Figure 17:
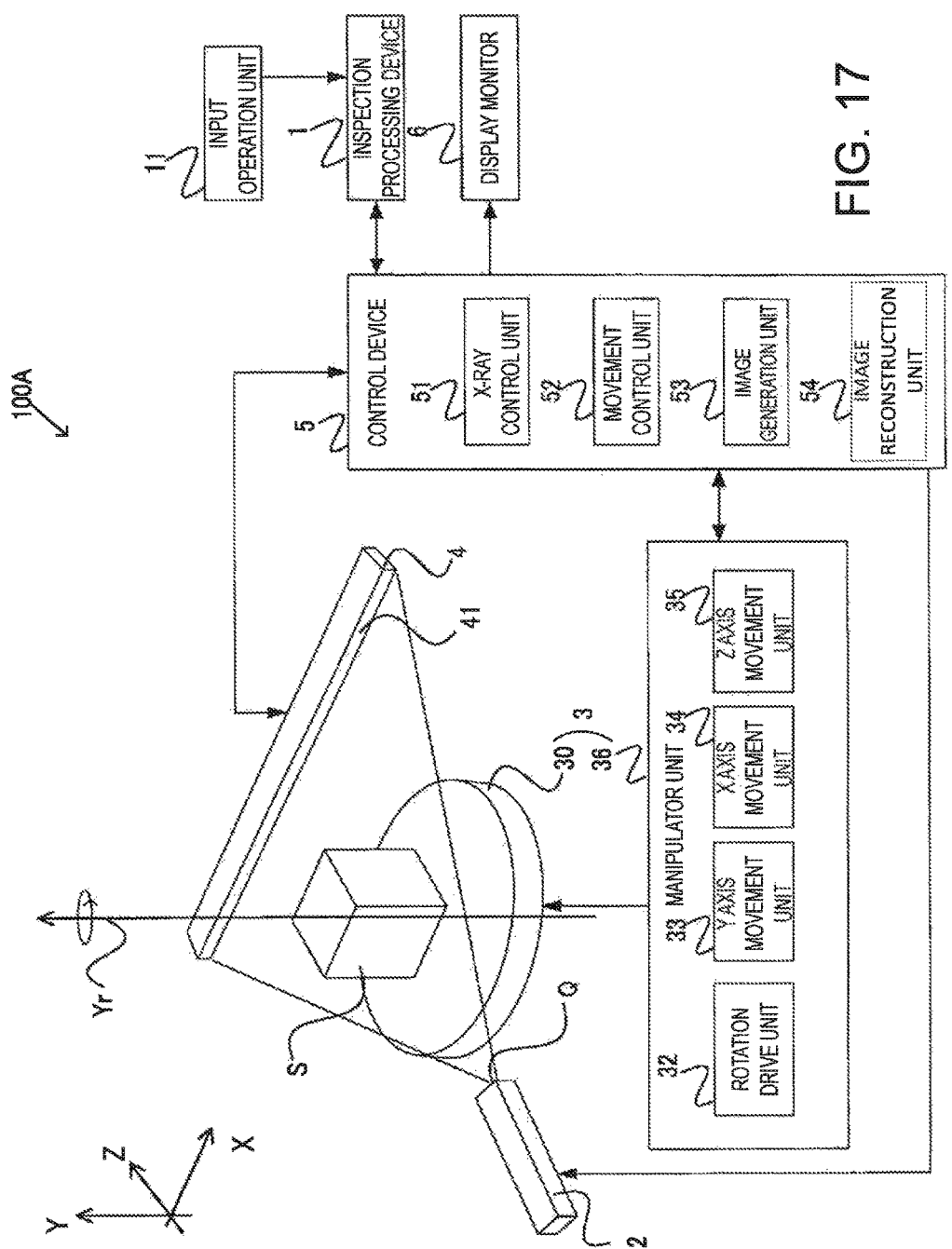
FIG. 17 is a diagram schematically illustrating an example of a configuration of an X-ray inspection device of a second embodiment.

FIG. 17 is a drawing schematically illustrating an example of a configuration of an X-ray inspection device 100A according to the second embodiment. As described above, the inclination adjustment unit 37 is not provided in a manipulator unit 36A of the placement unit 3. Other configurations are the same configurations as the X-ray inspection device 100 of the first embodiment illustrated in FIG. 1. Note that the master data M is generated in the same manner as the first embodiment.

—Inspection Process—

In the present embodiment, the X-ray inspection device 100A sequentially inspects a plurality of specimens S as described below.

First, the specimen S is placed on the placement stage 30. As described above, the specimen S is brought into contact with a positioning pin of the placement stage 30, and therefore, the specimen S can be positioned on the placement stage 30. Note that in the present embodiment, the inclination adjustment unit 37 is not provided. Therefore, the upper surface of the placement stage 30 is always parallel with the XZ plane.

The inspection range setting unit 115 sets the partial scan region of the specimen Sin a region including the inspection target region. In the present embodiment, even if the specimen S is in an inclined condition, the length (thickness) in the Y direction of the scan region is set to be longer (thicker) such that the inspection target region is included in the scan region of a single partial scan. In other words, the thickness of the partial scan region set in the present embodiment is thicker than the thickness of the thin sliced scan region in the first embodiment. The partial scan in the present embodiment is referred to as a thick sliced scan.

Next, a thick sliced scan of the specimen S is performed. The movement control unit 52 controls the manipulator unit 36 to rotationally drive and move the placement stage 30 in the Y direction. The region information acquisition unit 112 acquires region information obtained by the thick sliced scan.

The comparison unit 113 compares the region information acquired by the region information acquisition unit 112 based on the thick sliced scan with master data M stored in the data accumulation unit 117, and then based on the results thereof, identifies to which region in the master data region the thick sliced scan region corresponds. In other words, which part within the region of the master data M was thick slice scanned is identified.

Next, the positional difference calculation unit 114 extracts (selects) an extraction region including the inspection target region from region information acquired by the thick sliced scan, based on the positional relationship between the thick sliced scan region and the position of the inspection target region in the region of the master data M. The X-ray inspection device 100A is not provided with the inclination adjustment unit 37, and therefore, there are variations in inclination of the thick sliced scan region with regard to the plurality of specimens S, but the positional difference calculation unit 114 selects essentially the same position in the specimens S.

Next, the evaluation unit 116 evaluates the quality of the specimen S based on the extraction region. The evaluation results are stored in the data accumulation unit 117.

Figure 18:
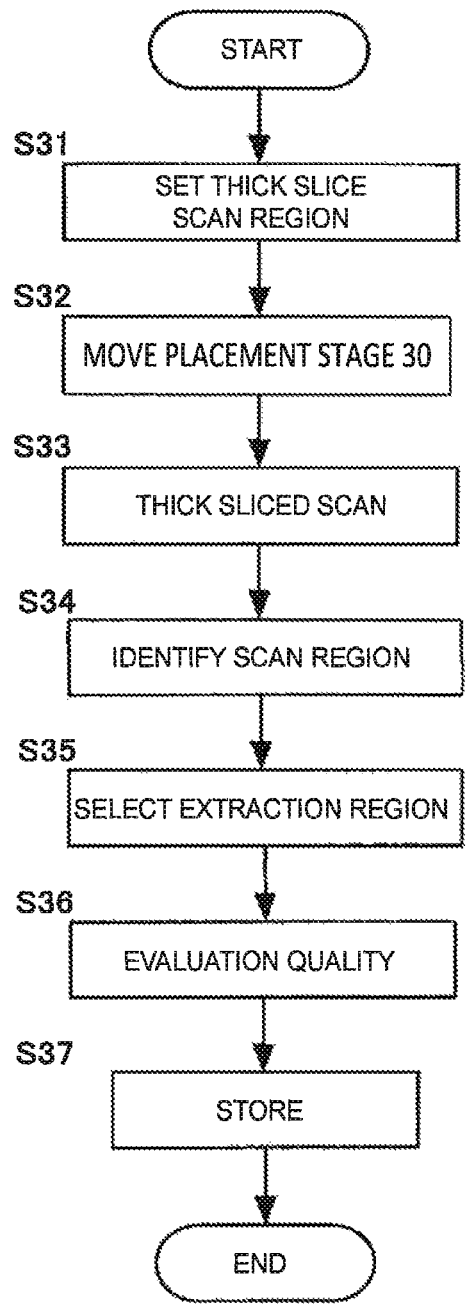
FIG. 18 is a flowchart describing an inspection process of the second embodiment.

A measurement process of the specimen S in the present embodiment will be described while referring to the flowchart in FIG. 18. A program for executing processes shown in the flowchart of FIG. 18 is stored in advance in a memory (not shown in the drawing), and is read and executed by a microprocessor of the inspection processing device 1. Note that the specimen S is placed on the placement stage 30.

In step S31, the inspection range setting unit 115 sets a thick sliced scan region, and the proceeds to step S32. In step S32, the control unit 110 instructs the movement control unit 52 to control the manipulator unit 36 to move the placement stage 30 to a movement start position for the thick sliced scan, and then proceeds to step S33. In step S33, the control unit 110 instructs the X-ray control unit 51 to control the X-ray source 2. The controller unit 110 instructs the movement control unit 52 to control the manipulator unit 36 to set the sliced plane, and rotate and move the placement stage 30 in the Y direction. Thereby, the thick sliced scan is performed, and then the process proceeds to step 34.

In the step S34, the comparison unit 113 compares region acquired by the thick sliced scan with the master data M stored in the data accumulation unit 117, identifies to which position in the master data region the thick sliced scan region corresponds, and then proceeds to step S35. In step S35, the positional difference calculation unit 114 selects an extraction region including the inspection target region from region information acquired by the thick sliced scan, based on the positional relationship between the thick sliced scan region and the position of inspection target region within the region of the master data M, and then proceeds to step S36.

In step S36, the evaluation unit 116 evaluates the quality of the specimen S based on region information in the extraction region, and then proceeds to step S37. In step S37, the data accumulation unit 117 stores information based on the thick sliced scan, information related to the positional relationship between the thick sliced scan region and the extraction region, and information related to evaluation results of the quality of the specimen S, and then completes the program.

—Evaluation of Quality of Specimen S—

The evaluation unit 116 evaluates the quality of the specimen S based on the region information obtained by thick sliced scanning the specimen S. As an evaluation procedure, the extraction region is divided into a unit three-dimensional lattice to form a lattice grid. In the present embodiment, the X-ray inspection device 100A is not provided with the inclination adjustment unit 37, and therefore, there are variations in inclination of the thick sliced scan region with regard to the plurality of specimens S. Therefore, the evaluation unit 116 forms a lattice grid with regard to the extraction region. In the plurality of specimens S, the extraction regions are the same, and as a result, the dividing positions and dividing directions of the grid are the same. In other words, for the plurality of sequentially inspected specimens S, the lattice grid 650 can be set at essentially the same position, and evaluations can be performed at the same position.

In the aforementioned second embodiment, the following effects are achieved in addition to the effects of the first embodiment.

(1) The comparison unit 113 selects the extraction region from the thick sliced scan region. Thereby, a lattice grid can be formed based on an inclination of the evaluation region in the thick sliced scan region, and therefore, the quality of the plurality of specimens S can be evaluated under the same conditions, and thus the reliability of the evaluation is improved.

(2) The thickness of the thick sliced scan was increased. Thereby, the inspection target region is included in the scan region, and therefore, the inspection target region can be reliably evaluated based on the single thick sliced scan, which contributes to improving productivity.

—Embodiment of Structure Manufacturing System—

An embodiment of a structure manufacturing system including the X-ray inspection device 100 according to the first embodiment or X-ray inspection device 100A according to the second embodiment will be described. The structure manufacturing system creates a molded product such as, for example, a door portion, an engine portion, or a gear portion of an automobile, or an electronic component that incorporates an electronic circuit board and the like. In the following description, the structure manufacturing system is described to be provided with the X-ray inspection device 100 described in the first embodiment, but the system is the same for a case provided with the X-ray inspection device 100A described in the second embodiment, and therefore, a description thereof is omitted.

Figure 19:
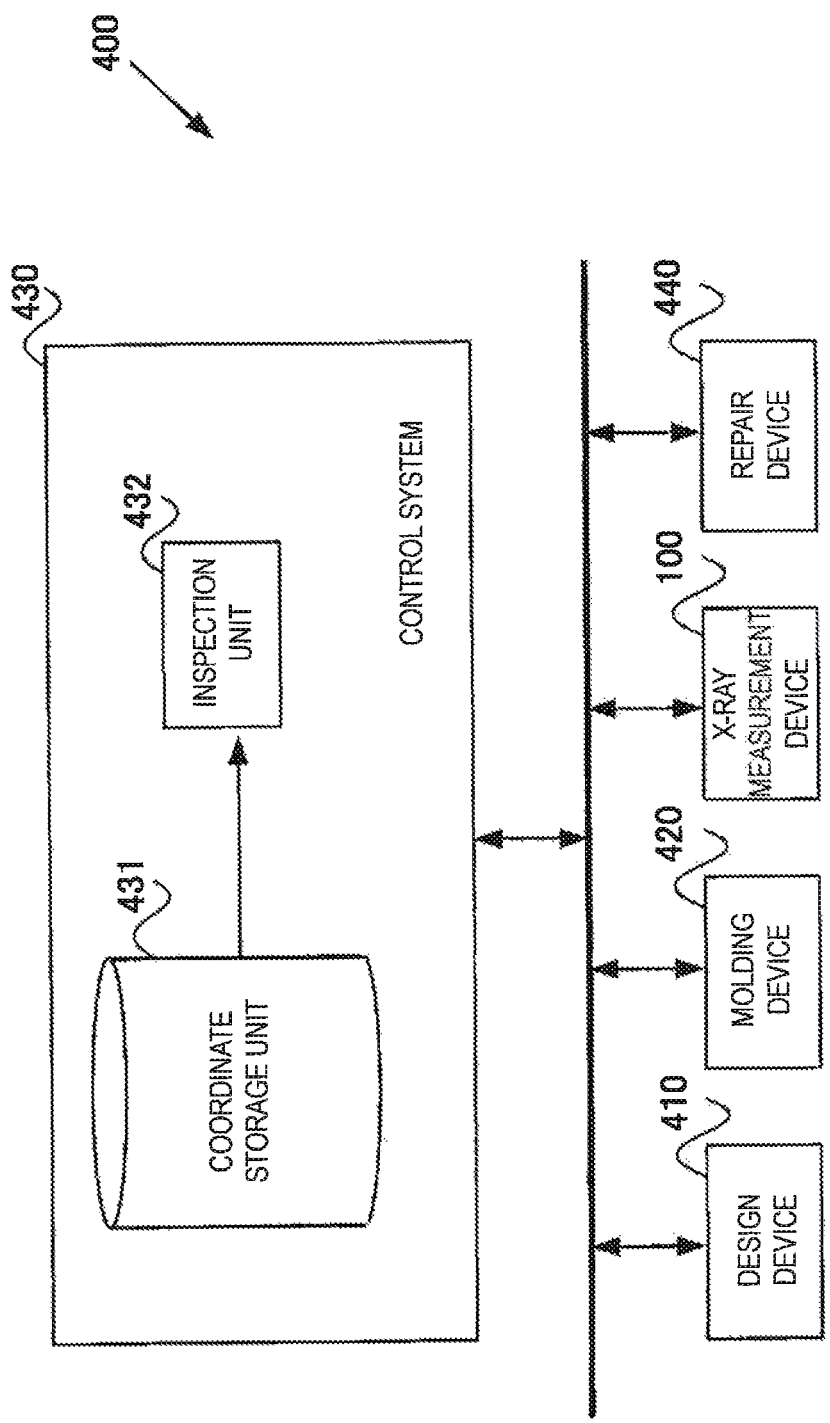
FIG. 19 is a block diagram illustrating an example of a configuration of a structure manufacturing system according to the embodiment.

FIG. 19 is a block diagram illustrating an example of a configuration of a structure manufacturing system 400 according to the present embodiment. The structure manufacturing system 400 is provided with the X-ray inspection device 100 described in the first embodiment, a design device 410, a molding device 420, a control system 430, and a repair device 440.

The design device 410 is a device used by a user when creating design information related to the shape of a structure, and performs a design process for creating and storing design information. The design information is information indicating coordinates of each position of the structure. The design information is output to the molding device 420 and the control system 430 described later. The molding device 420 performs a molding process for creating and molding the structure using the design information created by the design device 410. In this case, the molding device 420 that performs at least one of laminating process which is representative in 3D-printer technology, casting process, forging process, and cutting process is also included in one aspect of the present invention.

The X-ray inspection device 100 performs an inspection process for inspecting a shape of the structure molded by the molding device 420. The X-ray inspection device 100 outputs to the control system 430 information indicating a coordinate of the structure (hereinafter, referred to as "shape information"), which is an inspection result of inspecting the structure. The control system 430 is provided with a coordinate storage unit 431 and an inspection unit 432. The coordinate storage unit 431 stores the design information created by the aforementioned design device 410.

The inspection unit 432 determines whether or not the structure molded by the molding device 420 is molded according to the design information created by the design device 410. In other words, the inspection unit 432 determines whether or not the molded structure is a quality product. In this case, the inspection unit 432 reads the design information stored in the coordinate storage unit 431 and performs an inspection process of comparing S the design information and the shape information input from the X-ray inspection device 100. For example, as an inspection process, the inspection unit 432 compares a coordinate indicated by the design information with a coordinate indicated by corresponding shape information, and determines that the structure is a quality product molded if the result of this inspection process shows that the coordinate of the design information and coordinate of the shape information match. When the coordinate of the design information and the corresponding coordinate of the shape information do not match, the inspection unit 432 determines whether or not a difference between the coordinates is within a predetermined range, and determines that the structure is a repairable defective product if the difference is within the predetermined range.

When determined to be a repairable defective product, the inspection unit 432 outputs to the repair device 440 repair information indicating a defective site and amount of repair. The defective site is the coordinate of the shape information that do not match the coordinate of the design information, and the amount of repair is the difference between the coordinate of the design information and the coordinate of the shape information at the defective site. The repair device 440 performs a repair process for reprocessing the defective site of the structure based on the input repair information. The repair device 440 again performs a process similar to the molding process performed by the molding device 420 in the repair process.

Figure 20:
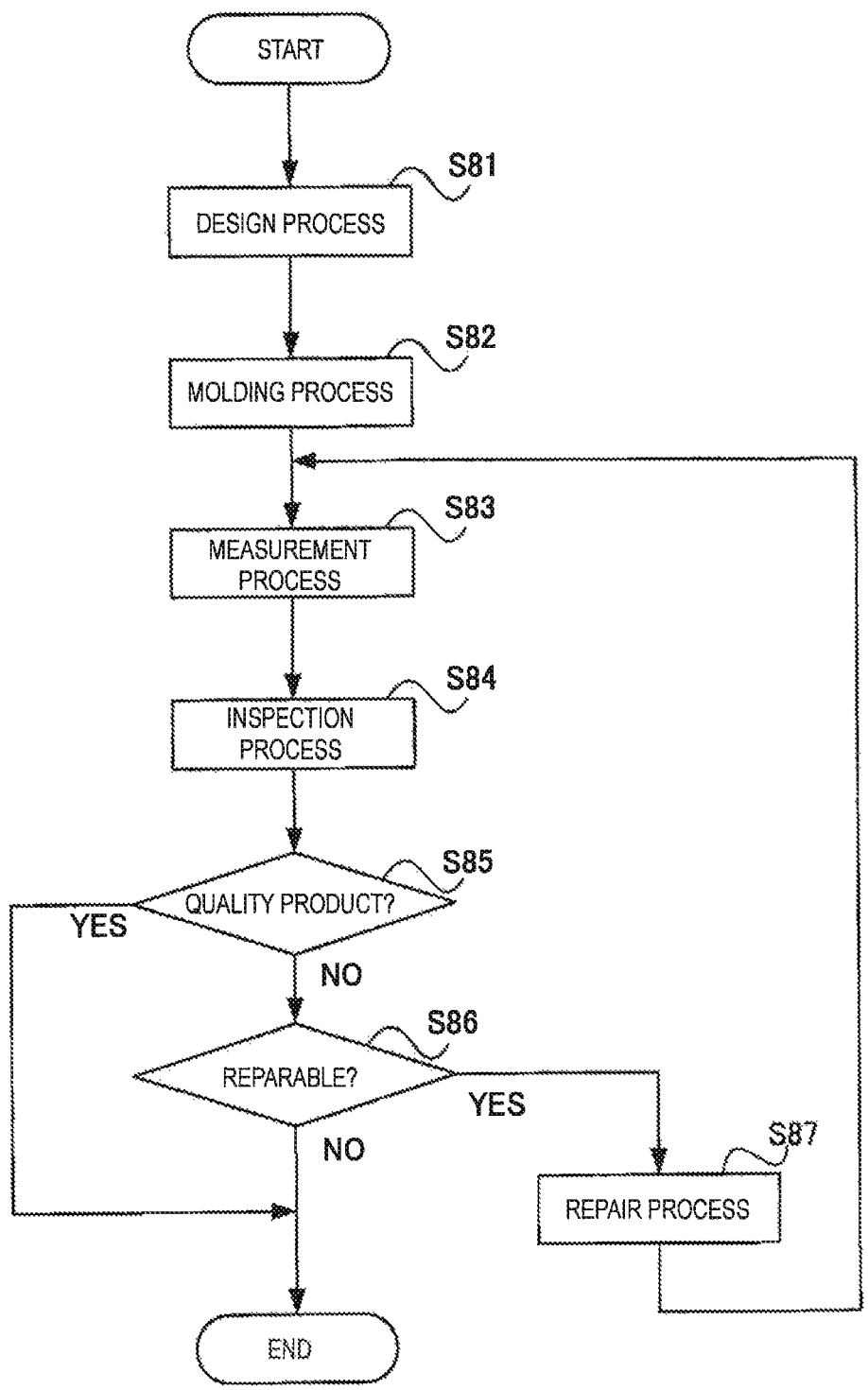
FIG. 20 is a flowchart describing a process of a structure manufacturing system.

The processing performed by the structure manufacturing system 400 will be described while referring to the flowchart illustrated in FIG. 20.

In step S81, the design device 410 is used when a user designs the structure, creates and stores design information related to the shape of the structure by the design process, and then proceeds to step S82. Note that the present invention is not limited to only the design information created by the design device 410, and if design information already exists, inputting the design information to acquire the design information is also included in one aspect of the present invention. In step S82, the molding device 420 creates and molds the structure based on the design information by the molding processing, and then proceeds to step S83. In step S83, the X-ray inspection device 100 performs the inspection process to measure the shape of the structure, outputs the shape information, and then proceeds to step S84.

In step S84, the inspection unit 432 performs the inspection process of comparing the design information created by the design device 410 and the shape information inspected and output by the X-ray inspection device 100, and then proceeds to step S85. In step S85, the inspection unit 432 determines based on the result of the inspection processing whether the structure molded by the molding device 420 is a quality product. If the structure is a quality product, in other words, if the coordinate of the design information and the coordinate of the shape information match, step S85 is determined to be affirmative, and thus the process ends. If the structure is not a quality product, in other words, if the coordinate of the design information and the coordinate of the shape information do not match or if a coordinate that is not present in the design information is detected, step S85 is determined to be negative, and the process proceeds to step S86.

In step S86, the inspection unit 432 determines whether the defective site of the structure is repairable. If the defective site is unrepairable, in other words, if the difference between the coordinate of the design information in the defective site and the coordinate of the shape information exceeds the predetermined range, step S86 is determined to be negative, and thus the process ends. If the defective site is repairable, in other words, if the difference between the coordinate of the design information in the defective site and the coordinate of the shape information is within the predetermined range, the step S86 is determined to be positive, and the process proceeds to step S87. In this case, the inspection unit 432 outputs the repair information to the repair device 440. In step S87, the repair device 440 performs the repair process on the structure based on the input repair information, and then returns to step S83. Note that as described above, the repair device 440 again performs a process similar to the molding process performed by the molding device 420 in the repair process.

The following effects are achieved with the aforementioned structure manufacturing system.

(1) The X-ray inspection device 100 of the structure manufacturing system 400 performs an inspection process of acquiring the shape information of the structure created by the molding device 420 based on the design process of the design device 410, and the inspection unit 432 of the control system 430 performs an inspection process of comparing the shape information acquired in the inspection process with the design information created in the design process. Therefore, inspection of a defect in the structure and information for the inside of the structure can be acquired by nondestructive inspection to determine whether or not the structure is a quality product created according to the design information, which contributes to quality management of the structure.

(2) The repair device 440 performs the repair process that again performs the molding process on the structure based on the comparison result of the inspection process. Therefore, a process similar to the remolding process can be performed on the structure if the defective portion of the structure is repairable, which contributes to manufacturing a structure of a high quality that is close to the design information.

Modifications as described below are also within the scope of the present invention, and it is also possible to combine one modified example or a plurality of modified examples with an embodiment described above.

(1) In the aforementioned description, the comparison unit 113 determines whether or not the thin sliced scan region corresponds to the inspection target region set by the inspection range setting unit 115, based on the reconstruction image obtained by the first partial scan and master data M stored in the data accumulation unit 117. In other words, the aforementioned description assumes that the thin sliced scan region is included in the master data region. However, when an error in the shape of the specimen S is larger than expected, or the thickness of the master data region is inadequate, the thin sliced scan region may deviate from the master data region. Therefore, before determining whether or not the thin sliced scan region corresponds to the inspection target region set by the inspection range setting unit 115, the comparison unit 113 may determine whether or not the thin sliced scan region is included in the master data region. Thereby, even if an error in the shape of the specimen S is larger than expected, or the thickness of the master data region is low and inadequate, for example, so long as the thickness of the scan region is increased and a partial scan is performed again to overlap the thicker partial scan region and master data region, the position of the thicker partial scan region can be identified, and thus a positional relationship with the evaluation region can be grasped.

(2) In the aforementioned second embodiment, the configuration is such that information used in evaluating the quality of the specimen S is obtained by a single thick sliced scan, but the configuration may be as follows. In other words, even if the inclination adjustment unit 37 is not provided in the manipulator unit 36A of the placement unit 3, a thin sliced scan may be performed as a single partial scan similar to the first embodiment.

Specifically, the same first thin sliced scan (partial scan) as the first embodiment is performed, and the positional difference between the first partial scan region and the inspection target region set by the inspection range setting unit 115 is calculated. Furthermore, a region including the evaluation region can be re-set as the target partial scan region based on the calculated positional difference, and a second partial scan is performed.

The inclination of the specimen S cannot be corrected because the inclination adjustment unit 37 is not provided, and therefore, the thickness of the target partial scan region when the second partial scan is to be performed is set such that the inspection target region is included even if the specimen S is inclined.

The operation of each unit for setting the target partial scan region when performing the first partial scan, for the first partial scan of the specimen S, and for processing when the first partial scan region is determined to correspond to the inspection target region is the same for the thin sliced scan of the first embodiment. When the first partial scan region is determined not to correspond to the inspection target region, the operation of each unit until a positional difference between a position of the inspection target region and a position in the specimen S corresponding to the region information acquired by the first partial scan is calculated is the same as the aforementioned first embodiment.

When a positional difference between the position of the inspection target region and position in the specimen S corresponding to the region information acquired by the first partial scan is calculated, the inspection range setting unit 115 sets the second partial scan region of the specimen S in a region including the inspection target region, based on the positional difference. The thickness of the target partial scan region when performing the second partial scan is so as to include the inspection target region even if the specimen S is inclined, as described above.

Next, the second partial scan is performed for the specimen S. As described above, the thickness of the target partial scan region is set such that the inspection target region is included in the partial scan region in the second partial scan, and therefore, the inspection target region is included in the second partial scan region.

The operation of each unit after the second partial scan is performed is the same as the operation of each unit after performing the thick sliced scan in the aforementioned second embodiment.

When configured in this manner, a case where a partial scan is performed twice occurs, but if the inclination or deviation in the Y direction caused by variations in the outline of the specimen S is large for example, the inspection time of one specimen S can be reduced as compared to a case where one thick sliced scan is performed as with the second embodiment. In other words, if the variation in the outline of the specimen S is large, and the inclination or deviation in the Y direction is large, then the thickness of the thick sliced scan is required to be large, and even with one partial scan, the inspection time may increase as compared to when performing a partial scan twice as described above.

Therefore, if the variation in the outline of the specimen S is large, the inspection time of one specimen S can be reduced as compared to the second embodiment, which effectively contributes to improving productivity.

(3) The aforementioned description was described such that the region SXa for the master data M includes the evaluation region 62, as illustrated in FIG. 4. However, when the specimen SX structure is simple near the evaluation region 62, a characteristic shape as described above is difficult to appear in the reconstruction image near the evaluation region 62, and therefore, identifying the position of the sliced plane is difficult.

In this case, the region SXa for the master data M is set to a location separated from the evaluation region 62, as illustrated in FIG. 5.

As illustrated in FIG. 5, if the master data region and the evaluation region to be inspected, in other words, the inspection target region is separated, information using the evaluation of the quality of the specimen S is acquired as follows.

First, the inspection range setting unit 115 sets the target partial region in a part of a region in the master data region. Next, the control unit 110 controls each unit so as to perform a first partial scan for the specimen S. The comparison unit 113 compares the region information acquired by the region information acquisition unit 112 based on the first partial scan with master data M stored in the data accumulation unit 117, and then based on the results thereof, identifies to which region in the master data region the first partial scan region corresponds.

If the position of the master data region to which the position of the first partial scan region corresponds is known, the difference between the position of the inspection target region and the position of the first partial scan region is also known. Therefore, the positional difference calculation unit 114 calculates a positional difference between the first partial scan region and inspection target region.

When the positional difference between the first partial scan region and the inspection target region is calculated, the movement control unit 52 controls the manipulator unit 36 to move the placement stage 30, such that the positional difference is zero. Thereby, the scan region of the second partial scan includes the inspection target region.

(4) In the aforementioned description, the positional relationship between the X-ray source 2 and/or detector 4 and specimen S is changed by the movement of the placement stage 30, but the X-ray source 2 and/or detector 4 may he moved without moving the placement stage 30 to change the positional relationship with the specimen S.

(5) The X-ray inspection device 100 may have an X-ray source that emits a cone beam, and a detector 4 that is not a line sensor and has a. structure where pixels are arranged two-dimensionally. In this case, a signal is preferably output from the pixels arranged in a line based on the sliced plane 700 from the detector 4. With this configuration, the sliced plane 700 can be displaced in a direction other than the Y direction.

(6) In the aforementioned description, if the master data M is generated from the specimen S initially inspected by the X-ray inspection device 100, the upper surface of the placement stage 30 is made parallel with the XZ plane, the specimen S is placed on the placement surface in a posture for X-ray inspection, and in this condition, the partial scan is performed while rotating the placement stage 30 to acquire shape information of the specimen S1 initially to be scanned. However, the following procedure may be adopted prior to generating the master data M.

Figure 11B:
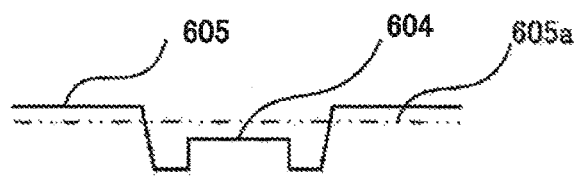
FIG. 11B is a diagram describing a surface reference.

As illustrated in FIG. 11A, a surface reference 604 is normally provided on the specimen S which is a cast product. The surface reference 604 is a region for setting a reference plane, and for example, the reference plane is set by three surface references. The reference plane is set as a reference for measuring the dimensions of a specimen. In a cast product such as an engine cylinder block, the surface reference 604 is set to a position deeper than a peripheral casting surface 605 as illustrated in FIG. 11B, and therefore, a surface of the surface reference remains without processing, even if a surface of the cast product is processed. For example, as illustrated in FIG. 11B, even if 605 which is a casting surface of a casting is processed to a plane as expressed by dotted and dashed line 605*a*, the height is set such that the surface of the surface reference 604 remains without processing.

When acquiring the measurement information of the specimen S1 initially to be scanned, first, the upper surface of the placement stage 30 is made parallel with the XZ plane, the specimen S1 initially to be scanned is placed on the placement stage 30, and the specimen S1 initially to be scanned is brought into contact with a positioning pin not illustrated in the drawings to position the specimen S1 initially to be scanned on the placement stage 30. In this condition, the three surface references 604 of the specimen S1 initially to be scanned are measured by a three-dimensional measurement instrument. Thereby, the inclination of the reference plane with regard to the placement surface can be calculated.

If the X-ray inspection device 100 has an inclination adjustment mechanism for the placement stage 30, the inclination adjustment mechanism operates to make the inclination of the reference plane with regard to the placement surface 30 zero. In other words, the inclination adjustment mechanism is operated to match a device coordinate system of the X-ray inspection device 100 and a coordinate system of the specimen S initially to be scanned. Thereafter, the partial scan is performed while rotating the placement stage 30 to generate the master data M from the specimen S initially to be scanned.

If the X-ray inspection device 100 does not have an inclination adjustment mechanism for the placement stage 30, the scan thickness when generating the master data M is set based on the inclination of the reference plane with regard to the calculated placement surface, and then the master data M is generated from the specimen S initially to be scanned by the already described procedure.

The three-dimensional measurement instrument may be a contact type three-dimensional measurement instrument or a non-contact type three-dimensional measurement instrument. Furthermore, the measurement instrument may be a three-dimensional measurement instrument installed inside the X-ray inspection device 100, or a portable three-dimensional measurement instrument.

Note that in the present embodiment, if the measurement target includes a reference site such as the surface reference or the like when measuring, the position can be calculated even if the surface reference and a sliced region other than the surface reference are connected or separated. However, in the present embodiment, if a reference part is not included in the measurement range, whether or not a region that is actually measured is the target region is not known. In some cases, a problem occurs where a region separated from the target region is measured. Therefore, a problem occurs where the same target regions cannot be measured for the plurality of specimens. In the present embodiment, the master data M is generated, and therefore, even if the reference site is not included, whether or not a measurement region is a target region is known. Furthermore, the position of the measurement region is compared with the master data M, and therefore, the position thereof can be determined.

The outline of the specimen S may be measured by a three-dimensional measurement instrument or the like in a condition where the surface reference 604 is received in a measuring jig after casting. In this case, the following procedure may be adopted prior to generating the master data M. In other words, if the outline is measured by a three-dimensional measurement instrument or the like in a condition where the surface reference 604 of the cast product is received in a measuring jig, measurements are performed for a surface on which the specimen S1 initially to be scanned is placed on the placement stage 30 of the X-ray inspection device 100. Thereby, the inclination of the placement surface during X-ray inspection with regard to a reference plane based on the surface reference 604 can be calculated.

After calculating the inclination of the placement surface with regard to the reference plane, a procedure of generating the master data M is the same as the procedure described above.

(7) In the aforementioned first embodiment, a point was, described where the master data M may be generated based on the outline shape of the specimen S obtained by an inspection device other than the X-ray inspection device 100. Specifically, the master data NI can be generated as follows.

Figure 21A:
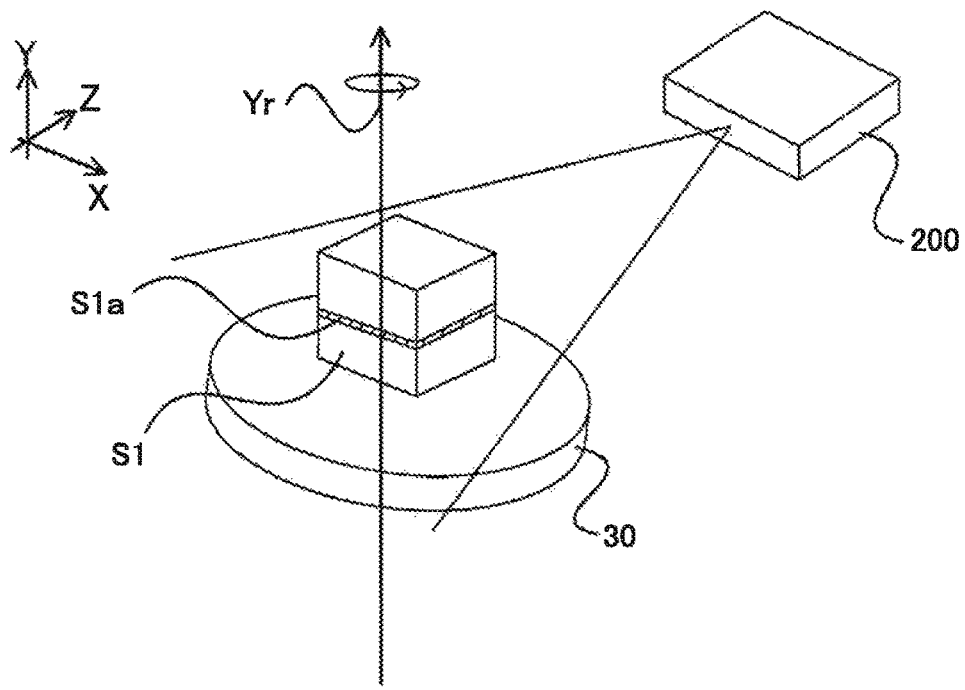
FIG. 21A is s conceptual diagram where outline measurement is performed for a thin region.

An upper surface of the placement stage 30 is made parallel with the XZ plane, for a part in the Y direction of the specimen S1 initially to be scanned placed on the placement stage 30, a plurality of outer circumferential points are measured by a non-contact type three-dimensional measurement instrument such as a portable three-dimensional measurement instrument 200 or the like (hereinafter, simply referred to as three-dimensional measurement instrument 200), while rotating the placement stage 30. This condition is illustrated in FIG. 21A. A measurement range S1*a* in the Y direction may be small. In other words, measurements are performed for a plurality of positions in a thin region in the Y direction to obtain outline information. Measurement results are acquired by the configuration information acquisition unit 111 illustrated in FIG. 2. The positional difference calculation unit 114 obtains first measurement results and information related to the inclination of the specimen S1 initially to be scanned in the design coordinate system based on design information. of the specimen S1 initially to be scanned, for example.

Figure 21B:
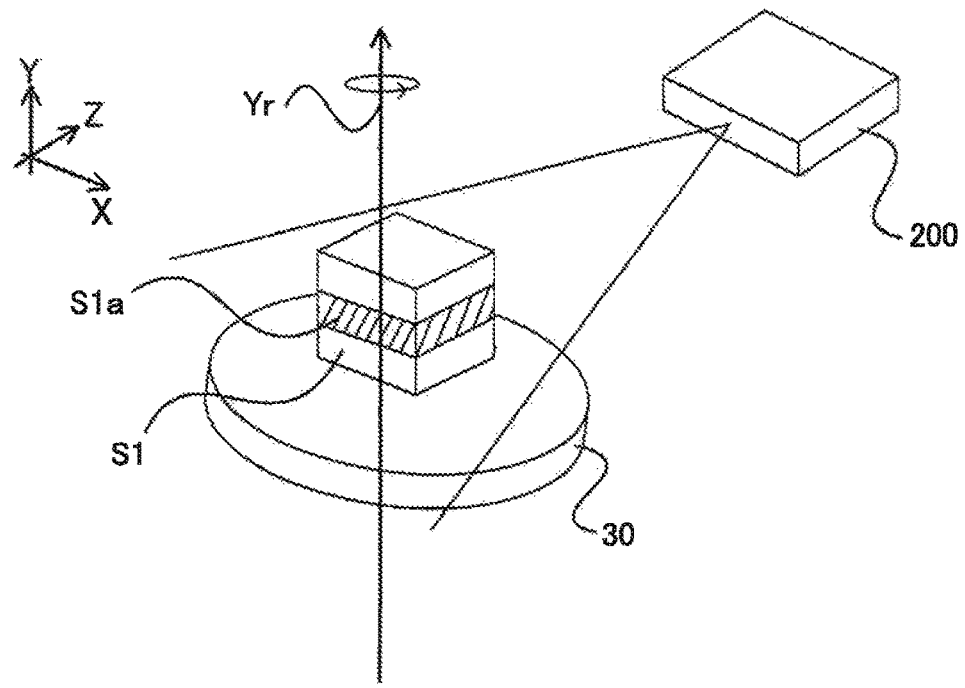
FIG. 21B is a conceptual diagram where outer shape measurement is performed for a thick region.

If an inclination adjustment mechanism is not provided in the placement stage 30, the inclination adjustment mechanism operates to make the inclination of the reference plane with regard to the placement surface zero. In other words, the inclination adjustment mechanism is operated to match a device coordinate system of the placement stage 30 and a coordinate system of the specimen S initially to be scanned. Thereafter, as illustrated in FIG. 21B, measurements are performed for the plurality of positions in a region with a predetermined thickness in the Y direction, by a three-dimensional measurement instrument 200, while rotating the placement stage 30. Master data is generated from the specimen S initially to be scanned based on the obtained measurement information.

If an inclination adjustment mechanism is not provided in the placement stage 30, the thickness in the Y direction when performing measurements by the three-dimensional measurement instrument 200 is set based on the obtained inclination information, and the measurements are performed for the plurality of positions. The master data M is generated from the specimen S initially to be scanned based on the obtained measurement information. If an inclination adjustment mechanism is not provided in the placement stage 30, the thickness in the Y direction is generally large. Note that when the specimen S1 initially to be scanned is measured by the three-dimensional measurement instrument 200, the specimen S1 initially to be scanned may be placed on another placement stage and not the placement stage 30 of the X-ray inspection device 100.

Therefore, if the master data M is data generated from information based on the outline shape of the specimen S obtained by an inspection device other than the X-ray inspection device 100, the outline shape for a part in the Y direction of the specimen S may be measured by the three-dimensional measurement instrument 200 in place of the thin sliced scan in the aforementioned first embodiment. Furthermore, a partial scan corresponding to the rescan in the first embodiment may be performed while referring to the measurement results by the three-dimensional measurement instrument 200.

(8) The inspection processing device 1 in the aforementioned embodiments or a function of a part of the inspection processing device in the modified example may be implemented by a computer. In this case, a program for implementing the control function may be recorded in a computer readable recording medium, and the program related to the aforementioned control, stored in the recording medium may be read and in a computer system and executed for implementation. Note that "computer system" as referred to herein includes an OS (operating system) and hardware for peripheral equipment. Furthermore, a "computer readable recording medium" refers to a flexible disk, magneto-optical disk, optical disk, memory card or other portable recording medium, a hard drive internally provided in the computer system, or other storage device. Furthermore, the "computer readable recording medium" may also include: a medium that dynamically maintains the program for a short amount of time such as a communication line when sending the program through the Internet or other network or a phone line or other communication line; or medium that maintains the program for a certain amount of time such as a volatile memory inside the computer system serving as a server or a client in this case. Furthermore, the aforementioned program may implement a part of the aforementioned function, and the function may be implemented by combining of the program with a program already recorded in the computer system.

Figure 22:
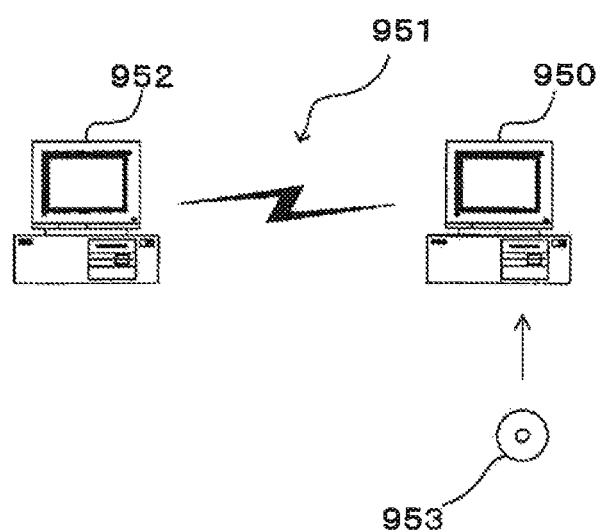
FIG. 22 is a diagram describing an entire configuration of an apparatus used to provide a program product.

Furthermore, when applied in a personal computer or the like, the program related to the aforementioned control can be provided through a CD-ROM or other recording medium or the Internet or other data signal. FIG. 22 is a diagram illustrating the condition. A personal computer 950 receives the program provided through a CD-ROM 953. Furthermore, the personal computer 950 has a connection function with a communication line 951. A computer 952 is a server computer that provides the aforementioned program and stores the program in a recording medium such as a hard disk or the like. The communication line 951 is the Internet, personal-computer communication, or other communication line, a dedicated communication line, or the like. The computer 952 reads the program using the hard disk and then sends the program to the personal computer 950 through the communication line 951. In other words, the program is transported by a carrier wave as a data signal and sent through the communication line 951. Therefore, the program can be provided as a computer-program product that can be read by a computer in various forms such as a recording medium or a carrier wave.

Figure 23:
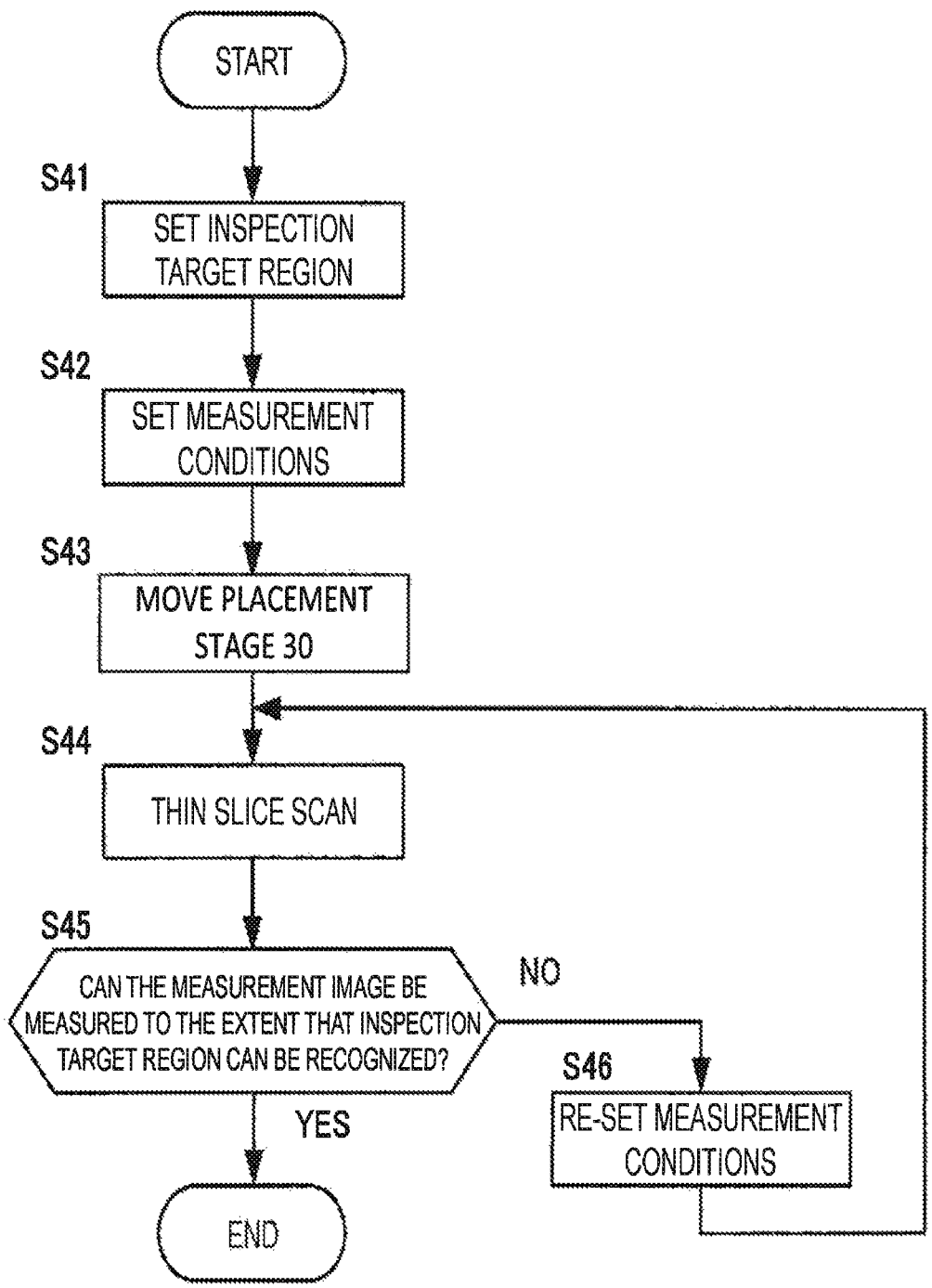
FIG. 23 is a flowchart describing setting measurement conditions based on the embodiment.

(9) Setting the measurement conditions of the X-ray inspection device 100 in the aforementioned examples will be described with reference of the flowchart shown in FIG. 23. Note that measurement conditions when the inspection target region in the aforementioned embodiments is selected and inspected will be described. For example, the X-ray inspection device 100 will be described. A case where the inspection target region is selected and the partial scan is performed will be described as an example. First, the inspection target region is set (S41). For example, when the inspection target region is selected, the X-ray inspection device 100 calculates a distance that emitted X-rays penetrate a specimen. For calculating the distance, for example, when the evaluation region is set as the inspection target region as described in PCT/JP2014/073096 and/or PCT/JP2014/073097, an optimum placement direction of a specimen is determined based on the total number of sliced planed with regard to a specimen S and the total amount of movement of the specimen S, such that the inspection time is reduced. Thereby, the distance that X-rays penetrate the specimen is calculated. The X-ray inspection device estimates the X-ray strength required beforehand based on the distance that the X-rays penetrate and material of the specimen. The accelerating voltage and current of the X-ray source emitting X-rays is estimated in order to achieve the estimated X-ray strength. Other than the estimated accelerating voltage and current of the X-ray source, an exposure time of a detector that detects X-rays penetrating the specimen may be used. Furthermore, in a target inspection, the measurement conditions of X-rays may be determined based on the magnitude of the defects.

Therefore, a thin sliced scan is performed using the estimated measurement conditions (S44). Prior to performing the thin sliced scan, the placement stage 30 is moved to move the specimen to a predetermined position. Note that the measurement conditions of the X-rays may be set before or after moving the placement stage 30. Next, a projected image or reconstruction image is created after performing the thin sliced scan. Whether or not the created projected image or reconstruction image is optimal for performing inspection is estimated (S45). For example, if inspecting defects (fine spaces) in the internal structure, an outline structure or outline part of the internal structure only is clearly recognizable, but if the magnitude of a defect in the internal structure cannot be sufficiently recognized, then the measurement conditions are again re-set (S46). For example, the exposure time is increased such that the magnitude of the defect in the internal structure can be recognized. Furthermore, for example, if a defect in the internal structure can be recognized by adjusting the contrast of the projected image and reconstruction image, image contract adjustment may be performed, thereby making remeasurements using X-rays unnecessary.

Note that measurement conditions sufficient for penetrating the subject may be calculated regardless of the placement direction of the subject using full scan or design information of the subject, and the subject may be measured using the calculated measurement conditions.

Furthermore, a part of PCT/JP2014/073096 and/or PCT/JP2014/073097 may be incorporated and used.

The above described embodiments are examples, and various modifications can be made without departing from the scope of the invention.

What is claimed is:

1. A measurement processing device, comprising:
    a memory storing instructions; and
    at least one processor configured to execute the instructions to:
    acquire a first sliced region that is a part of a specimen, as first sliced region information, by using X-rays; and
    identify a position of the first sliced region in the specimen, by using the first sliced region information and shape information of the specimen.

2. The measurement processing device according to claim 1, wherein the at least one processor is further configured to execute the instructions to:
    store the shape information of the specimen.

3. The measurement processing device according to claim 1, wherein the shape information is design information of the specimen.

4. The measurement processing device according to claim 1, wherein the shape information is measurement information in which a first specimen with a structure equivalent to the specimen is measured by using the X-rays.

5. The measurement processing device according to claim 1, wherein the shape information is measurement information in which a first specimen with a structure equivalent to the specimen is measured by a measurement other than using the X-rays.

6. The measurement processing device according to claim 1, wherein the shape information is information related to a partial region of the specimen.

7. The measurement processing device according to claim 1, wherein the at least one processor is further configured to execute the instructions to:
    identify the position of the first sliced region in the specimen by comparing the shape information of the first sliced region with the shape information of the specimen.

8. The measurement processing device according to claim 7, wherein the wherein the at least one processor is further configured to execute the instructions to:
    acquire a region to be inspected as the first sliced region; and
    calculate a positional difference between a position of the region to be inspected and a position of the first sliced region.

9. The measurement processing device according to claim 8, wherein the at least one processor is further configured to execute the instructions to:
    determine whether or not the calculated positional difference is within a predetermined range; and
    instruct a further measurement of the specimen by using X-rays in case the positional difference is larger than the predetermined range.

10. The measurement processing device according to claim 1, wherein an evaluation region for evaluating a quality of the specimen is set; and
    the evaluation region that is set is acquired as the first sliced region.

11. The measurement processing device according to claim 1, wherein a sliced region of the specimen included in the shape information is thicker than the first sliced region.

12. The measurement processing device according to claim 11, wherein the sliced region of the specimen included in the shape information is thicker than the first sliced region in a direction orthogonal to a region surrounded by a light-emission point of the X-rays and is configured to acquire the first sliced region and a detection region to detect the X-rays passed through the specimen.

13. An X-ray inspection device, comprising:
    the measurement processing device according to claim 1;
    an X-ray source that emits X-rays on the specimen;
    wherein at least one processor configured to execute the instructions to:
    detect the X-rays passed through the specimen.

14. A structure manufacturing method, comprising:
    creating design information related to a structure shape;
    creating the structure based on the design information;
    acquiring shape information by measuring the shape of the created structure, using the measurement processing device according to claim 1; and
    comparing the design information and shape information acquired above.

15. A measurement processing method, comprising:
    acquiring a first sliced region that is a part of a specimen, as first sliced region information, by using X-rays; and
    identifying a position of the first sliced region in the specimen by using the first sliced region information and shape information of the specimen.

16. A measurement processing method, the measurement processing method comprising:
    acquiring first sliced region information related to a first sliced region that is a part of a specimen, by using X-rays; and
    identifying a position of the first sliced region in the specimen, based on the first sliced region information and the shape information of the specimen for identifying a position of the first sliced region in the specimen.

17. A control device, comprising:
    a memory storing instructions; and
    at least one processor configured to execute the instructions to:
    send information related to a position of first sliced region information in the specimen to a display monitor, the information being identified by comparing the first sliced region information that is a part of a specimen acquired by using X-rays with shape information of the specimen.

18. The control device according to claim 17, wherein the first sliced region information is a first sliced region image representing the first sliced region, and the shape information is a shape image representing a shape of the specimen; and wherein at least one processor configured to execute the instructions to:

identify a position of the first sliced region in the specimen by using the first sliced region image and the shape image.

19. The control device according to claim 18, wherein a shape included in the first sliced region is obtained from the first sliced region image, and wherein at least one processor configured to execute the instructions to:

identify the position of the first sliced region information in the specimen.

20. The control device according to claim 17, wherein the shape information is design information of the specimen.

\* \* \* \* \*